(12) United States Patent
Francavilla et al.

(10) Patent No.: US 8,851,091 B2
(45) Date of Patent: Oct. 7, 2014

(54) CONTACT LENS CLEANING SYSTEM WITH MONITOR

(75) Inventors: Charles Francavilla, Fremont, CA (US); Ramin Najafi, Novato, CA (US); Eddy Low, Foster City, CA (US); Timothy Shiau, Oakland, CA (US); Eric Douglas Turtle, Belmont, CA (US); Donogh John Roger O'Mahony, Sn Mateo, CA (US)

(73) Assignee: NovaBay Pharmaceuticals, Inc, Emeryville, CA (US)

( * ) Notice: Subject to any disclaimer, the term of this patent is extended or adjusted under 35 U.S.C. 154(b) by 118 days.

(21) Appl. No.: 13/403,754

(22) Filed: Feb. 23, 2012

(65) Prior Publication Data

US 2012/0211027 A1    Aug. 23, 2012

Related U.S. Application Data

(60) Provisional application No. 61/445,910, filed on Feb. 23, 2011, provisional application No. 61/547,598, filed on Oct. 14, 2011.

(51) Int. Cl.
| | |
|---|---|
| *B08B 3/00* | (2006.01) |
| *A61L 12/00* | (2006.01) |
| *A61L 12/12* | (2006.01) |
| *C11D 3/39* | (2006.01) |
| *C11D 3/00* | (2006.01) |
| *G02C 13/00* | (2006.01) |

(52) U.S. Cl.
CPC .............. *C11D 3/0078* (2013.01); *A61L 12/128* (2013.01); *C11D 3/3947* (2013.01); *G02C 13/008* (2013.01); *Y10S 134/901* (2013.01)
USPC ............ 134/113; 134/901; 422/300; 422/301

(58) Field of Classification Search
None
See application file for complete search history.

(56) References Cited

U.S. PATENT DOCUMENTS

| | | |
|---|---|---|
| 2,409,073 A | 10/1946 | Sias et al. |
| 2,985,949 A | 5/1961 | Rice |
| 3,912,451 A | 10/1975 | Gaglia, Jr. |
| 3,942,981 A | 3/1976 | Sato |
| 4,186,392 A | 1/1980 | Holz |

(Continued)

OTHER PUBLICATIONS

Martin et al.; Measurement of the temperature profile of an exothermic autocatalytic reaction front; Phys Rev E; 80; pp. (055101R)1-4; Nov. 19, 2009.

(Continued)

*Primary Examiner* — Nicole Blan
(74) *Attorney, Agent, or Firm* — Brian Clarke; Clarke IP Law

(57) ABSTRACT

The invention monitors the neutralization process involving hydrogen peroxide solution and a hydrogen peroxide neutralization catalyst and compares measured values with theoretical values. The system monitors the chemical reaction and notifies the user of the neutralization status. In an exemplary embodiment, the initial hydrogen peroxide solution concentration is neutralized with a palladium catalyst after a period of time. A microcontroller analyzes the measurements and displays the neutralization process results using colored LED lights and/or text or images on a LCD display. In one embodiment, an apparatus adapted for use with a cleaning solution used to clean a medical device may include a trigger, a processing device in communication with the trigger, and a display device. The processing device provides a trigger count and the display device communicates with the processing device and displays a message based on the count.

31 Claims, 22 Drawing Sheets

(56) References Cited

U.S. PATENT DOCUMENTS

| | | | | |
|---|---|---|---|---|
| 4,395,139 | A | 7/1983 | Namiki et al. | |
| 4,588,307 | A | 5/1986 | Palti | |
| 4,636,091 | A | 1/1987 | Pompei et al. | |
| 4,637,919 | A | 1/1987 | Ryder et al. | |
| 4,687,997 | A * | 8/1987 | Tao | 324/439 |
| 4,736,191 | A | 4/1988 | Matzke et al. | |
| 4,750,610 | A * | 6/1988 | Ryder | 206/5.1 |
| 4,784,149 | A | 11/1988 | Berman et al. | |
| 4,797,840 | A | 1/1989 | Fraden | |
| 4,993,419 | A | 2/1991 | Pompei et al. | |
| 5,012,813 | A | 5/1991 | Pompei et al. | |
| 5,129,999 | A | 7/1992 | Holland et al. | |
| 5,145,323 | A | 9/1992 | Farr | |
| 5,184,633 | A | 2/1993 | Langford | |
| 5,186,317 | A | 2/1993 | Ryder et al. | |
| 5,196,174 | A | 3/1993 | Cerola et al. | |
| 5,238,369 | A | 8/1993 | Farr | |
| 5,280,834 | A | 1/1994 | Berkley | |
| 5,302,345 | A | 4/1994 | Oksman et al. | |
| 5,328,597 | A * | 7/1994 | Boldt et al. | 210/87 |
| 5,366,078 | A | 11/1994 | Braun | |
| 5,518,591 | A | 5/1996 | Pulliainen et al. | |
| 5,558,846 | A | 9/1996 | Alvord et al. | |
| 5,609,284 | A | 3/1997 | Kondratenko | |
| 5,609,837 | A | 3/1997 | Cerny et al. | |
| 5,650,597 | A | 7/1997 | Redmayne | |
| 5,653,238 | A | 8/1997 | Pompei | |
| 5,699,900 | A | 12/1997 | Artis | |
| 6,148,992 | A | 11/2000 | Kanner et al. | |
| 6,183,705 | B1 * | 2/2001 | Chang | 422/301 |
| 6,653,842 | B2 | 11/2003 | Mosley et al. | |
| 7,129,717 | B2 * | 10/2006 | Donsky | 324/692 |
| 7,682,269 | B1 | 3/2010 | Gait | |
| 8,603,252 | B2 * | 12/2013 | Dimeo et al. | 134/1.1 |
| 2006/0070956 | A1 * | 4/2006 | Herrmann et al. | 210/744 |
| 2007/0284263 | A1 | 12/2007 | Giardina et al. | |
| 2008/0179200 | A1 | 7/2008 | O'Hara et al. | |
| 2009/0211925 | A1 | 8/2009 | Doniga | |
| 2010/0093019 | A1 * | 4/2010 | Ditcham et al. | 435/34 |
| 2010/0259719 | A1 | 10/2010 | Sabeta | |
| 2011/0028807 | A1 | 2/2011 | Abreu | |

OTHER PUBLICATIONS

PCT Written Opinion of the ISA PCT/US2012/026249.

* cited by examiner

CONTACT LENS CLEANING SYSTEM WITH MONITOR

CROSS REFERENCE TO RELATED APPLICATIONS

The present application claims the benefit of U.S. Provisional Application Nos. 61/445,910, filed on Feb. 23, 2011 and 61/547,598, filed Oct. 14, 2011. The foregoing applications are hereby incorporated by reference herein in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to system for cleaning and disinfecting contact lenses and method of use thereof. In various respects, the invention is directed to a system that monitors the cleaning solution neutralization process using a reaction sensor and compares the measured values with theoretical values. The invention determines if the process is proceeding properly or not, based on the measurements obtained by the reaction sensor, and notifies the user of the status of the neutralization.

BACKGROUND

There are two main types of chemical disinfection systems for contact lenses, multipurpose and hydrogen peroxide-based systems. Hydrogen peroxide-based systems are often preferred, due to its rapid kill of microbial contaminants, preservative-free packaging, low user sensitivity, and neutralization to natural by-products, such as water and oxygen. The disadvantage of the hydrogen peroxide-based systems are that they require memorization of what time the disinfection time was started and figuring out when the neutralization process is complete. Also, if too much time has elapsed since the hydrogen peroxide solution has been neutralized, the sterile solution can eventually become re-infected and foster microbial growth. One of the main reasons why users switch from hydrogen peroxide-based systems to multipurpose is because hydrogen peroxide-based systems require users to calculate when the ideal usage time is for each time that they disinfect their contact lenses, without knowledge of how effective the platinum catalyst is working; that is, enough elapsed time has passed to ensure the peroxide has been fully neutralized, to avoid chemical conjunctivitis and keratitis, and short enough elapsed time to ensure microbes have not re-infected the sterile solution.

An example of a contact lens cleaning and sterilization system is described in U.S. Pat. No. 4,687,997. This cleaning system requires insertion of the lenses into a disinfecting solution for a preset time period followed by insertion into a neutralizing solution for a second preset time period. A first indicator shows a steady light while the disinfectant is in the cleaning case and a second indicator when the neutralizing solution is in the case. The system distinguishes the disinfecting solution from the neutralizing solution by measuring the electrical conductivity of the solution within the cleaning case. After a predetermined amount of time, both lights flash to indicate the item has been disinfected and neutralized, respectively. This system does not monitor the efficacy of cleaning, disinfecting or neutralization of the solutions, however; the indicator lights flash to show completion of the disinfecting and neutralization cycles solely in response to the passage of time.

Another example of a cleaning and sterilization system is described in U.S. Pat. No. 6,183,705. The system uses ultrasonic waves to clean contact lenses, and heat to disinfect contact lens solution medium. The system includes a housing, control circuit assembly, ultrasonic waveguide, a heating rod with two electrodes and a graduated cleaning cup that is operated using the automatic control circuit. The control circuit includes a microprocessor for controlling the heating rod and the ultrasonic waveguide. The microprocessor operates the ultrasound transducer for a preset time, then stops. After a rest time, the microprocessor heats the cleaning solution to a preset temperature of 90° C. as measured by a temperature sensor, then turns off the heating rod, allowing the lenses to soak in the hot solution for another preset time. Once again, this system does not monitor the efficacy of the cleaning solution; the cleaning process always proceeds along the same preset time intervals, and the indicator lights merely show which stage the cleaning process is in.

SUMMARY OF THE DISCLOSURE

The present invention uses a hydrogen peroxide solution for cleaning and disinfecting soft (hydrophilic) and rigid gas permeable contact lenses, and uses a platinum disk for peroxide neutralization. Neutralization is required to convert hydrogen peroxide to water and oxygen, so the residual solution on the contact will not irritate the eye during contact lens insertion. The system monitors the cleaning solution within the device, and guides the user through the contact lens cleaning process with lights and/or textual directions.

The system may also monitor the internal and external temperatures and verify that the hydrogen peroxide solution is neutralizing properly. The monitoring is done by verifying the exothermic peroxide-neutralization process is occurring at an acceptable rate. Causes of poor neutralization can include old or expired peroxide solution, poorly stored cleaning solution, extreme solution temperatures, or the platinum disc has decreased catalytic ability. The device can determine if the user accidently used a bottle of saline solution, instead of a bottle of hydrogen peroxide solution. If a bottle of saline solution is used instead of a bottle of hydrogen peroxide solution, the cleaning and disinfection of the contact lenses will not occur, increasing the risk of infection of the eye. Additionally, the device minimizes the desire to rinse the contacts with saline solution after cleaning and prior to insertion in to the eye; if hydrogen peroxide was mistakenly used instead of saline solution, chemical conjunctivitis or keratitis may result.

The present invention generally relates to an apparatus for cleaning and disinfecting contact lenses. Provided herein are apparatus, systems and methods for use with a cleaning solution used to clean a medical device in which one or more messages are displayed to encourage compliance with the normal medical device cleaning protocol.

The following embodiments, aspects and variations thereof are exemplary and illustrative which are not intended to be limiting in scope.

In one embodiment, a contact lens cleaning system includes a contact lens holder; a vial adapted to contain the contact lens holder and a cleaning solution; a reaction sensor adapted to monitor a chemical reaction rate of the cleaning solution; a processing device in communication with the reaction sensor to receive a reaction signal from the reaction sensor; and a display in communication with the processing device, the processing device being adapted to operate the display to provide cleaning efficacy information based on the reaction signal. A catalyst element may be disposed within the vial and adapted to react with the cleaning solution. The reaction sensor may be a temperature sensor. The temperature sensor may be disposed in a cap covering the vial or outside of the vial. The processing device may be adapted to determine a temperature change rate from the reaction signal.

In an embodiment, the system may determine cleaning efficacy by comparing the temperature change rate to a theoretical temperature change rate. The system may include an ambient temperature sensor disposed outside of the vial and may measure a temperature of air surrounding the vial. The processing device may display cleaning efficacy information based on a temperature signal from the ambient temperature sensor. The system may include a use counter communicating with the processing device. The processing device may display information corresponding to the number of cleaning uses of the cleaning system.

The reaction sensor may be a pressure sensor. The system may include a caddy to support the vial. The display may be disposed within the caddy. The display may be disposed in a cap on the vial. The system may include a solution sensor disposed within the vial. The processing device may determine the presence of cleaning solution within the vial based on a signal from the solution sensor. The solution sensor may include an electrode and/or a capacitive sensor.

In another embodiment, a method for cleaning a contact lens and displaying cleaning efficacy information includes receiving a contact lens into a contact lens holder, receiving cleaning solution into a vial, wherein the vial containing the contact lens and contact lens holder, determining a chemical reaction rate of the cleaning solution and cleaning efficacy information based on the chemical reaction rate, and displaying the cleaning efficacy information.

The vial may also contain a catalyst and the chemical reaction rate may include a rate of chemical reaction between the cleaning solution and the catalyst. The determining step may include monitoring temperature, monitoring temperature of the cleaning solution, monitoring temperature exterior to the vial, calculating a temperature change rate, comparing the temperature change rate to a theoretical temperature change rate, and/or monitoring temperature within the vial.

The method may include monitoring ambient temperature outside of the vial, such that the determining step includes determining the chemical reaction rate from the temperature within the vial and the ambient temperature. The method may include counting a number of contact lens cleaning uses and may display information related to the number of contact lens cleaning uses. The determining step may include monitoring pressure within the vial. The method may include determining whether there is cleaning solution in the vial prior to the step of determining a chemical reaction rate.

In another embodiment, the apparatus may include a cap assembly configured to attach to a contact lens cup, a contact lens holder extending from the cap assembly into the cup, a solution sensor attached to the cap assembly and configured to determine the presence of a solution within the cup, and a first temperature sensor attached to the cap assembly, a display and a microcontroller within the cap. The microcontroller may communicate with the solution sensor, the first temperature sensor and the display.

The solution sensor may be a pair of electrodes that measures conductivity or a capacitive sensor. The apparatus may include a catalyst for neutralizing the solution and the solution may be hydrogen peroxide. The first temperature sensor may be a thermocouple or a thermistor and may be positioned to measure a temperature of the solution or of air surrounding the cup.

The apparatus may include a second temperature sensor. A second temperature sensor may be positioned to measure a temperature of air surrounding the cup and may communicate with the microcontroller. The microcontroller may be adapted to receive conductivity data from the electrodes, solution temperature data from the first temperature sensor, and air temperature data from the second temperature sensor. The microcontroller may output a signal based on the data.

The signal output by the microcontroller may drive an LED on the display and may provide a text display on the display.

The text display may be provided through a liquid crystal display. A capacitive touch sensor may be attached to the cap assembly. The apparatus may include a battery for powering the microcontroller.

In another embodiment, a method for cleaning a contact lens and displaying a status of the cleaning process may include receiving a contact lens into a contact lens holder. A contact lens cleaning solution may be received into a contact lens cup, and a determination is made whether there is cleaning solution in the cup. If cleaning solution is present in the cup, the method may include measuring the temperature of the cleaning solution. The status of the cleaning may be determined based on the cleaning solution temperature. The status of the cleaning may be displayed.

The temperature of air surrounding the cup may be measured. The status of the cleaning may be determined based on the measured air temperature and displayed on an LED display. The status may be displayed on a message display. Determining the status of the cleaning may include measuring conductivity within the cup. Monitoring of the cleaning solution may be initialized by a capacitive touch sensor.

In another embodiment, an apparatus for cleaning and disinfecting contact lenses may include a cap assembly, a contact lens holder, a cleaning solution, a catalyst, a first temperature sensor, a display, and a microcontroller. The cap assembly is configured to attach to a contact lens cup. The contact lens holder extends from the cap assembly into the cup. The cleaning solution is contained within the cup. The catalyst is contained within the cup and configured to neutralize the cleaning solution. The first temperature sensor is attached to the cap assembly. The microcontroller is within the cap and communicates with the first temperature sensor and the display.

In another embodiment, there is provided apparatus, systems and methods for use with a cleaning solution used to clean a medical device in which one or more messages are displayed. The messages may inform the user about the cleaning protocol or the condition of the cleaning system, and may encourage compliance with proper cleaning protocols, including messages about when it is safe to use the medical device, when a cleaning system should be replaced, and, in some cases, to consult a healthcare professional.

Another embodiment provides for an apparatus which is adapted for use with a cleaning solution used to clean a medical device, the apparatus including a trigger, a processing device in communication with the trigger and which provides a count of the number of times the trigger has been tripped, and a display device in communication with the processing device wherein the display device displays a message based on the count. In certain embodiments, the medical device can be a contact lens. For example, the display device can display the message "Please replace your case and solution" when a certain count has been reached, for example when the count is 180, which would be the count at six months of daily use.

Another embodiment provides for an apparatus which is adapted for use with a cleaning solution used to clean a medical device and may include a sensor that measures a property of the cleaning solution or a nearby area or the medical device; a processing device in communication with the detector; a display device in communication with the processing device, wherein the display device displays a message based on the property of the cleaning solution or a nearby area or the medical device. In certain embodiments, the cleaning solution comprises hydrogen peroxide. In certain embodiments, the medical device is a contact lens. In certain embodiments, the sensor is a temperature sensor, an electronic sensor, a pressure sensor, a sound sensor, an optical sensor, or a gas sensor. In certain embodiments, the processing device compares an input signal from the sensor to one or more preset values, and provides one or more output signals depending on the comparison to the display device. In certain embodiments, the display device is a light (e.g. an LED) or a liquid crystal display.

Another embodiment provides for an apparatus which is adapted for use with a cleaning solution used to clean a medical device, comprising a temperature sensor that measures the temperature profile of the cleaning solution or nearby area during the cleaning cycle; a processing device in communication with the temperature sensor and storing in memory an acceptable temperature profile range; a timer; and a display device in communication with the processing device, wherein different messages are displayed on the display device depending on whether the temperature sensor measures a temperature profile that falls within or outside of the acceptable temperature profile range.

Another embodiment provides for an apparatus which is adapted for use with a cleaning solution used to clean a medical device and which provides a message to a user, comprising a means for measuring a property of the cleaning solution or a nearby area or the medical device; a processing means for (a) accepting an input signal; (b) providing a comparison of the input signal to one or more preset values; and (c) providing one or more output signals depending on the comparison; and a means for displaying a message, wherein the message is based on the output signal.

Another embodiment provides for a method of monitoring patient compliance with a protocol for cleaning a medical device with a cleaning solution, the method comprising obtaining data by measuring a property of the cleaning solution or a nearby area or the medical device, and displaying one or more messages according to the data. In some embodiments, the data may be provided to a medical professional.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
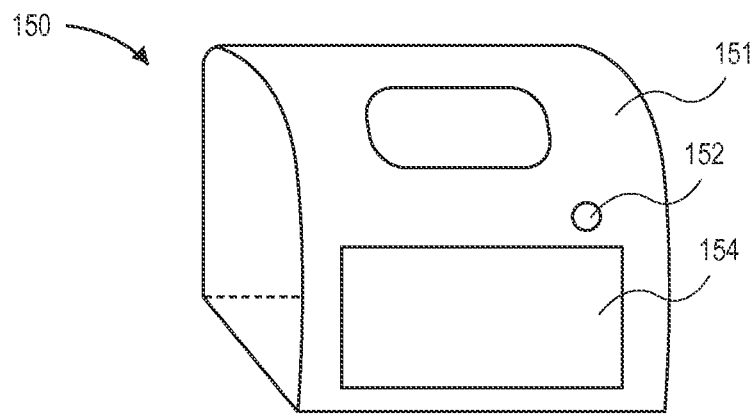
FIGS. 1A-1B illustrate an exemplary contact lens storage system.

The present invention relates to a system and method for monitoring the efficacy and status of a contact lens cleaning process, such as in systems using hydrogen peroxide and a neutralizing catalyst. One goal of the invention is to provide the user with an improved determination of when the catalyst has reduced the peroxide concentration low enough to allow insertion of the contact lenses into the eye. The improved determination, which traditionally was done solely based on elapsed time and uncorrected for solution temperature, may greatly reduce the risk of chemical conjunctivitis cause by accidental peroxide burns of the eye. Accidental burns may be caused by incorrect usage of the hydrogen peroxide disinfection system, the use of expired peroxide solutions, poorly stored disinfection solution, extreme disinfection solution temperatures, rinsing contacts with hydrogen peroxide prior to insertion, or the use of a platinum catalyst which has decreased catalytic ability.

Without knowledge of how effective the platinum catalyst is at neutralizing the cleaning solution, users may need to calculate when the safe usage time is for each instance that they disinfect their contact lenses. That is, the user may need to determine when enough time has elapsed to ensure the peroxide has been fully neutralized, to avoid chemical conjunctivitis, and short enough elapsed time to ensure microbes have not re-infected the sterile solution. The present invention automatically does the calculations for the user, so the user does not have to; and the device evaluates the effectiveness of the chemical reaction that is taking place during the neutralization.

The syystem includes a cap assembly configured to attach to a contact lens cup or vial. Examples of cleaning cases that include a cap and contact lens cup or vial are well known in the literature and may include other features not shown herein. Examples of such cases can be found in U.S. Pat. Nos. 4,637,919, 4,750,610, 5,186,317, 5,366,078, 5,558,846, 5,609,284, 5,609,837, and 6,148,992. Commercial examples of such cases are found in or included as parts of the AOSEPT® Disposable Cup & Disc (CIBA VISION®) and CLEAR CARE® (CIBA VISION®) systems.

A solution sensor may be attached to the cap assembly and configured to determine the presence of a solution within the cup. In some embodiments, the system may include a reaction sensor. The reaction sensor may be adapted to monitor a chemical reaction rate of the cleaning solution. The reaction sensor may be implemented as a temperature sensor, an electric sensor, a pressure sensor, a sound sensor, an optical sensor, or a gas sensor. The system may include a first temperature sensor attached to the cap assembly and a display. A first temperature sensor may be implemented as a first reaction sensor and may be configured to measure the temperature of the solution. The system may further include a second reaction sensor in the form of a second temperature sensor configured to measure the temperature of the air surrounding the cup. The cap assembly may include a microcontroller. The microcontroller may communicate with a reaction sensor, the solution detector, the capacitive touch sensor, the solution sensor, the first temperature sensor, a second temperature sensor, and/or the display, and send an output signal based on the data.

In certain aspects, the apparatus, systems and methods described herein may have the following advantages. In certain aspects, they may provide a convenient reminder to the user regarding whether cleaning is occurring or progressing normally, when it is safe to use the medical device, or when the medical device should be replaced. In embodiments where the apparatus, system or methods are used with a contact lens cleaner, they may improve user compliance with the procedures of cleaning contact lenses as well as improve safety and cleanliness of the lenses. In certain aspects, using the apparatus, systems and methods described herein may increase the likelihood that lenses have been cleaned properly, may decrease the likelihood that contact lenses will be re-infected after the cleaning procedure, or may decrease the likelihood that lenses will irritate the eye after being cleaned. For example, for apparatus in which hydrogen peroxide-based cleaning solutions are used, the apparatus described herein may indicate to the user if the solution is potent (that is, if there is sufficient peroxide in the solution to clean the lens within the specified time), if the normal cleaning cycle is complete and the lenses are safe to be placed in the eye, if the catalyst used to consume hydrogen peroxide is functioning properly or needs to be replaced, and other aspects of the cleaning protocol. In yet other aspects, apparatus described herein for use with a contact lens cleaning system may display a signal or message that the user should consult his or her optician or eye-care professional. In certain aspects, using the contact lens storage systems described herein may increase patient or user compliance with the normal lens cleaning protocol or other aspects of his or her eye care. Although some of the aforementioned advantages pertain to contact lens cleaning systems, these advantages may also pertain to corresponding apparatus, systems and methods adapted to be used to clean other medical devices, including dentures, endoscopes, catheters, ports, and so forth.

The term "caddy" refers to an apparatus adapted for use with a cleaning solution used to clean a medical device. In certain embodiments, a caddy may be an apparatus into or onto which a separate cleaning case may be removably placed. In other embodiments, a caddy may also be the cleaning case, i.e. cleaning solution may be poured directly into parts of the caddy.

The term "cleaning solution" refers to any liquid cleaning or disinfecting solution used to clean medical devices such as contact lenses. Cleaning solutions may or may not include hydrogen peroxide or other peroxide compounds. Cleaning solutions may also include other ingredients. Examples of cleaning solutions which may be used in accordance with the systems described herein include, without limitation, AOSEPT® Disinfectant (CIBA VISION®) and CLEAR CARE® (CIBA VISION®).

The term "cleaning system" refers to a cleaning solution and accompanying devices, such as a catalyst used to consume hydrogen peroxide in peroxide-based cleaning solutions.

The term "property" refers to a physical, chemical, electrical, optical, or other property, as well as a profile of that property over time.

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

Figure 1B:
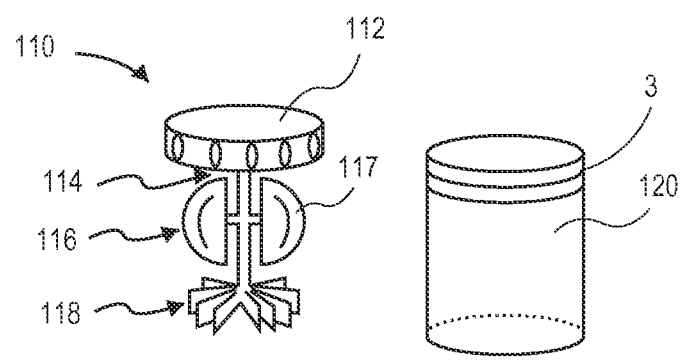

FIGS. 1A-B show caddy 150 and cleaning case 110. Referring to FIG. 1A, caddy 150 comprises caddy case 151, indicator 152, and display panel 154. Caddy case 151 may be made out of an appropriate material, e.g. a plastic or similar type of material, which is well known in the art. Indicator 152 may be a light or an LED (light emitting diode), and display panel may be an LCD (liquid crystal display) or a similar display panel capable of displaying text and/or graphical images either in color or black/white/grayscale. A display may be an indicator such as a light or an LED or a display panel such as an LCD. These components and structures are also well known in the art.

In some embodiments, caddy 150 may include a mechanism for providing an audio indication of the solution status, temperature monitoring, and other information. For example, caddy case may include one or more speakers and a controller or processor. The one or more speakers may output audio from an acoustic signal provided by the controller or processor. The controller or processor may receive temperature or other data from one or more sensors. An audio message may be provided based on the data provided by the sensors. For example, the caddy 150 may provide an audio alert indicating the time remaining in the neutralization process, the neutralization process is complete, the caddy is disinfecting the contact lens, disinfection was successful or unsuccessful, the solution is not detected and other messages. Hence, the system of the present invention may provide audio alerts in place or in addition to visual or tactive alerts to communicate events or conditions related to contact lens, the solution, and other aspects of the present technology.

Referring to FIG. 1 B, a separate and partially disassembled cleaning case 110 is shown. Cleaning case 110 may comprise such elements as cap 112, support beam 114, basket 116 and catalyst 118, and cylinder 120. Contact lenses, 117, are also shown. Examples of cleaning cases are well known in the literature and may include other features not shown herein, or modifications of the features shown herein. As shown, cleaning case 110 may be fully assembled by reversibly affixing (e.g. by screwing, snapping, form-fitting, friction fitting, etc.) cap 112 onto cylinder 120. The cylinder 120 of the embodiment illustrated in FIG. 1B includes threads or screws 3 for affixing cap 112. The cylinder 120 of the embodiment illustrated in FIG. 1B includes threads or screws 3 for affixing cap 112. Once fully assembled, the cleaning case may be removeably placed in or on the caddy.

Figure 2A:
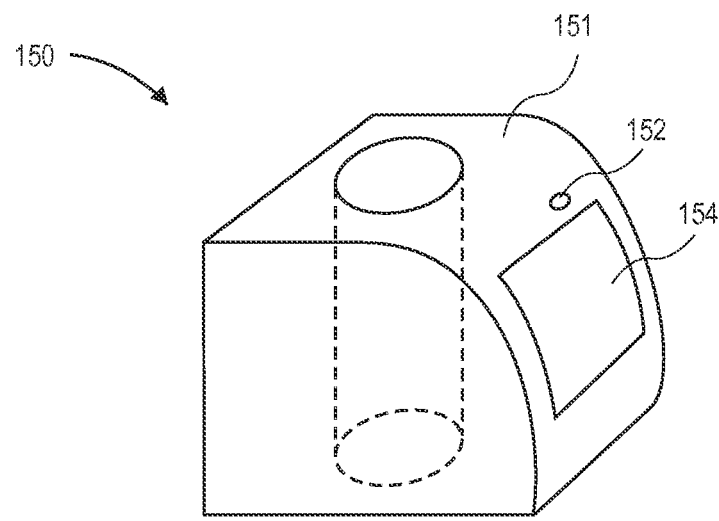
FIGS. 2A-2B illustrate another exemplary contact lens storage system.
Figure 2B:
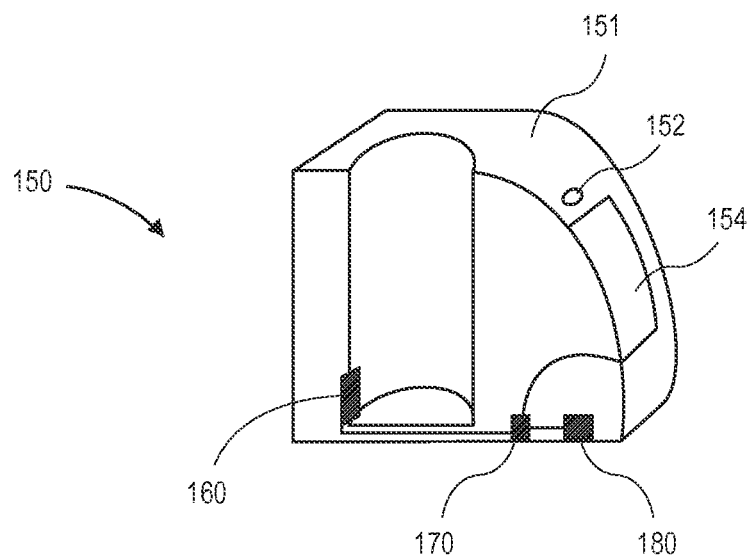

Referring to FIG. 2A, caddy 150 is shown in perspective side view, in which caddy case 151, indicator 152, and display panel 154 are also shown. FIG. 2B shows a cross-sectional view of caddy 150 and trigger 160, which are electronically connected to processing device 170, which is connected to and powered by power source 180. Processing device 170 is also electronically connected to indicator 152 and display panel 154. Trigger 160 is positioned such that it is tripped under normal operation when cleaning case 110 is placed in or on caddy 150. Tripping the trigger advances a counter within the processing device to provide a count. Processing device 170 may be a logic circuit, integrated circuit chip, or microprocessor, e.g. computing chip, or a plurality or combination thereof. Similarly, a processor may take the form of a logic circuit, integrated circuit chip, or microprocessor, e.g. a computer chip, or a plurality or combination thereof. Power source 180 may be a battery, e.g. a rechargeable battery or other type of battery typically used in small electronic devices. In some embodiments, the power source may be a power source external to the caddy, e.g. a household 110 V or similar source. A small transformer, not shown, may also be needed.

Figure 3:
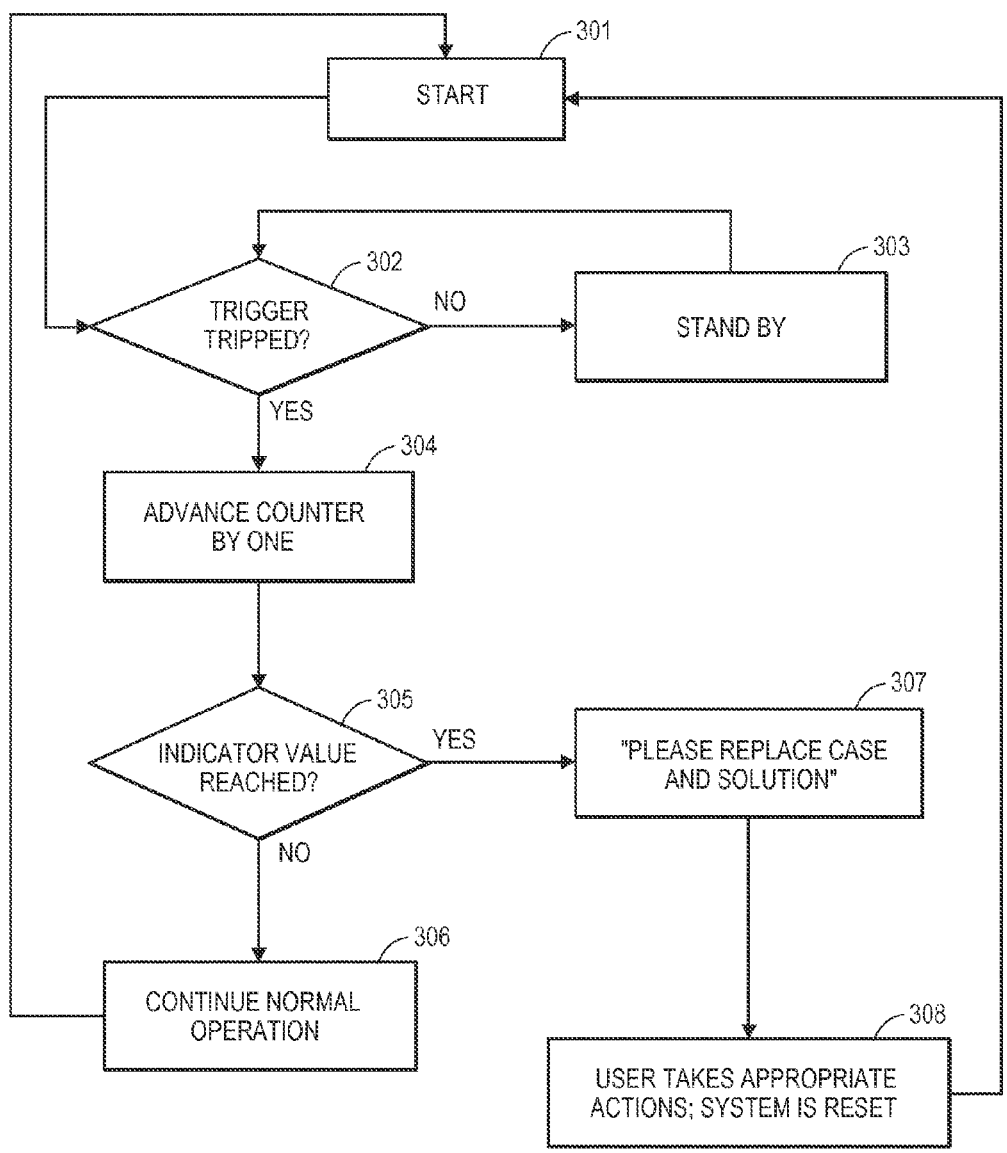
FIG. 3 illustrates an exemplary operational flowchart.

Referring to FIG. 3, various aspects of operation of certain embodiments of a caddy are shown. The process begins at step 301 after contact lenses and cleaning solution are placed in a cleaning case (e.g. cleaning case 110, FIG. 1A). At this time, the fully assembled cleaning case should be placed into the base unit. A trigger (e.g. trigger 160, FIG. 2B) and the processing device to which it is connected (e.g. processing device 170, FIG. 2B) can be used to determine if the contact lens case has been placed into the base unit at step 302. If a cleaning case has been placed therein, then a counter in the processing device may advance the count by one at step 304; if not, then the system may be placed in "stand by" mode at step 303. If the count reaches a certain preset indicator value at step 305, then the system can display a message such as "Please replace case and solution" at step 307. The preset indicator or other values may be stored in a memory unit, which may be part of the processing device.

For example, if lens cleaning cases and solutions typically have a useful life of about six months, then the indicator value can be set at 180 (assuming daily cleaning for six months). Other indicators values can be set, multiple indicators can be set for different messages, and the indicator values can be changed. When the count reaches an indicator value, the system can display an appropriate message to the user to encourage use of a new cleaning case and solution, thereby improving compliance with proper lens cleaning protocols. This procedure is represented by step 308. At this time, the systems can be reset, i.e. the counter can be reset to a zero value, for example by the user depressing a button or switch on the base unit (not shown) or via an external computing device (also not shown). Referring back to step 305, if the indicator has not yet been reached, then the user can continue normal operation of the cleaning system and may use it for a subsequent cleaning at step 306.

Messages may be in the form of a light, such as that from an LED or similar light, an audible signal such as a chime, bell, voice recording, etc., a tactile signal such as a Braille dot, or indicators displaying other signals. In one embodiment, when an indicator value in a processing device is reached, a red light is displayed. In another embodiment, a green light is displayed before the indicator value is reached, and when the indicator value is reached, the green light is turned off and a red light is on. Similarly, an audio signal such as a bell, chime, or suitable voice recording can be triggered when the indicator value is reached.

Messages may also take the form of a text message or graphical depiction, which may be displayed on an LCD. One example of a text message is "Please replace your case and solution" which can be displayed when a counter reaches a certain preset value, indicating that the solution and/or catalysts may be nearing the end of its useful lifetime. One example of a graphical depiction is a graphical representation of a cleaning case or a bottle of cleaning solution. More examples and details of messages are described below.

Additional examples of messages include the following: "Thank You for using Clear Care Lens Solution;" "You can trust your eyes to AOSEPT®;" "Your contact lenses are being disinfected;" "It will take six hours before your contact lens are ready for use;" "Your contact lenses are ready for use;" "Please remove them only after you have washed your hands with soap and water;" "Please discard your contact lens solution as the solution is no longer active;" "It is now six months since your contact lens case was purchased. Please see your Optometrist."

In various embodiments, a contact lens storage system can measure a property of (a) the cleaning solution, (b) the area near the cleaning solution (also referred to as a nearby area) (e.g. the gaseous headspace above the cleaning solution) or (c) one or more of the medical devices being cleaned. Examples of properties of the cleaning solution include temperature, electrical conductivity, color, UV/Vis absorbance, and profiles thereof (e.g. temperature vs. time, etc.). Examples of properties of the nearby area include pressure, sound (e.g. sound generated by bursting bubbles at the solution/air interface), temperature, and profiles thereof. Examples of properties of the medical devices include diffraction, dispersion or other property. Such measurement can, via known calculations and/or comparisons in a processing device, be the basis of one or more messages relating to whether the cleaning solution is potent, working properly, needs to be replaced, if the lenses are clean and ready to be removed for use, etc.

Figure 4A:
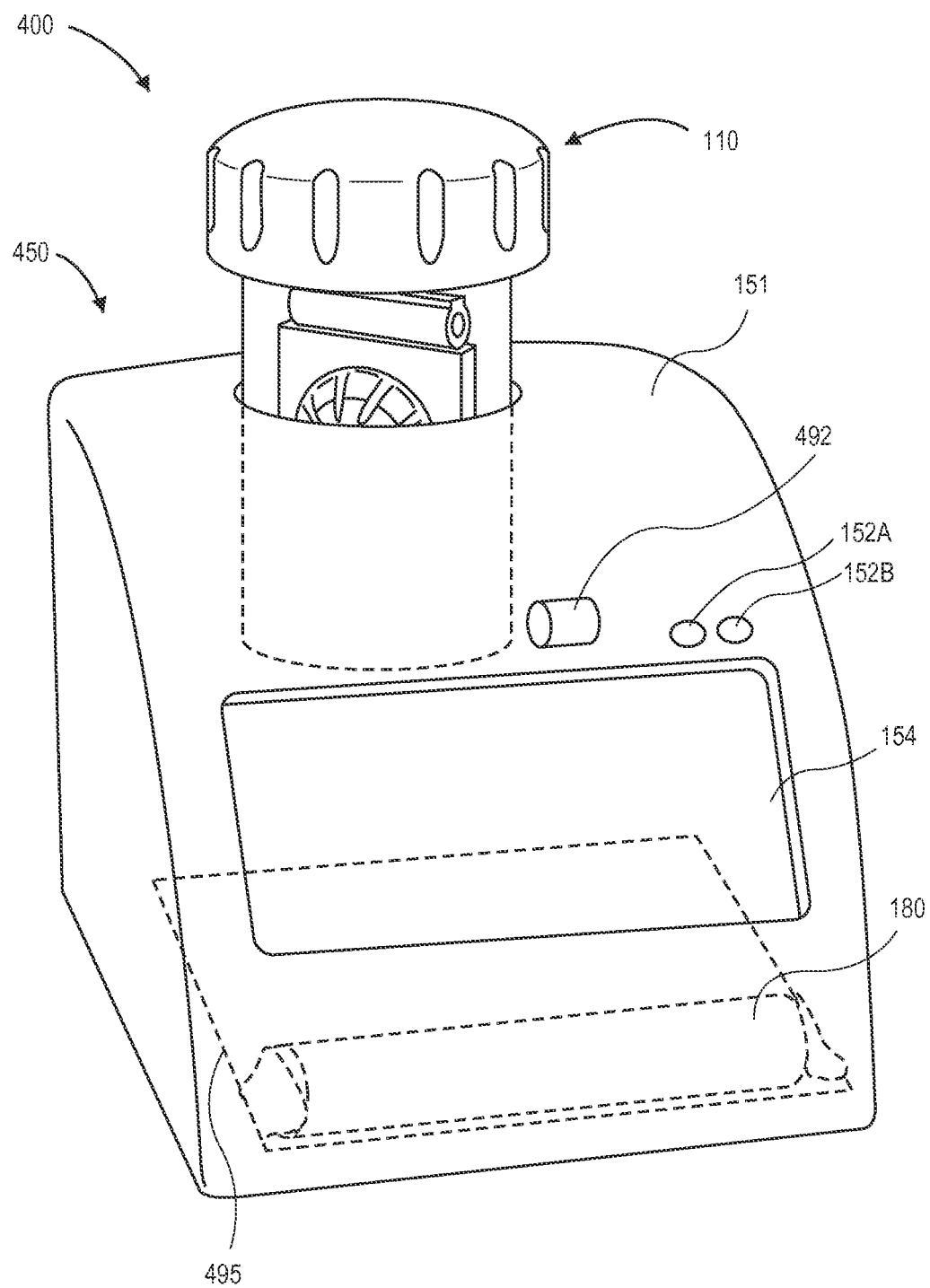
FIGS. 4A-4B illustrate another exemplary contact lens storage system.
Figure 4B:
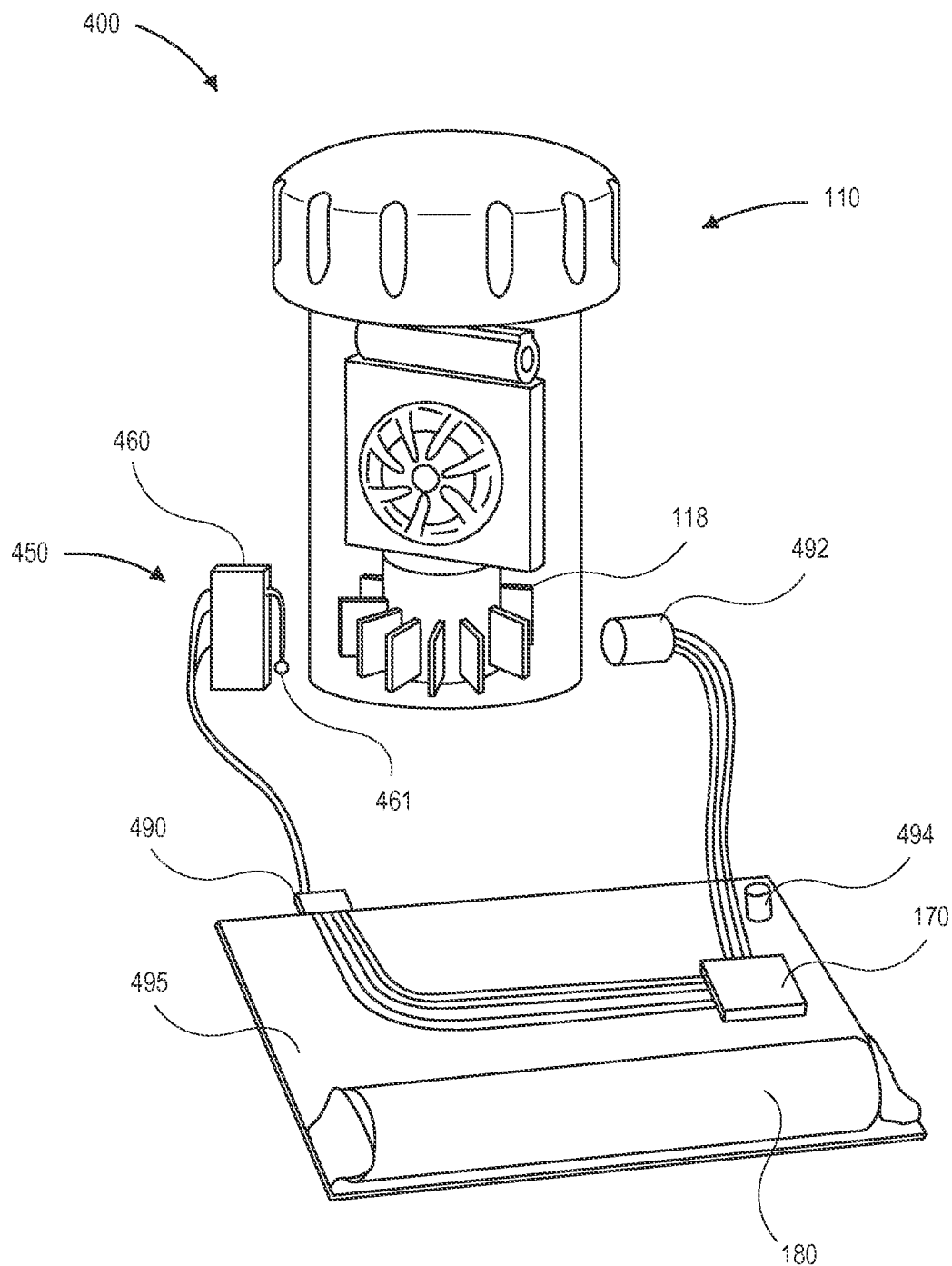

FIGS. 4A and 4B illustrate an embodiment of a contact lens storage system 400, showing cleaning case 110 removeably placed in base unit 450 (also referred to as a caddy herein). Referring to FIG. 4A, in this embodiment, base unit case 151 (also referred to as a caddy case herein) and display panel 154 are shown, as described above. Also in this embodiment, there are two indicators 152A and 152B which may be, for example, a red light and a green light, as described above. Depicted by dotted lines in this view are power source 180 (described above), temperature sensor 492, and circuit board 495.

FIG. 4B shows cleaning case 110 removeably placed in base unit 450 of contact lens storage system 400 in a view in which certain features are hidden from view and certain other features are described herein. Upon insertion of cleaning case 110 into the base unit 450, trigger 460 may be tripped and roller 461 may be deflected downward. Roller 461 may be a ball, disc, or similar component. Trigger 460 may be, for example, a mechanical switch (such as shown in FIG. 4B) or an optical switch such as a combination of a LED IR emitter and photo detector (not shown). Temperature sensor 492 may be situated such that it can monitor the temperature or temperature changes (i.e. temperature profile) of the cleaning solution during the cleaning cycle. Optional thermistor, 494, may be present in certain embodiments to measure the nearby temperature (e.g. the temperature external to the cleaning case). Trigger 460 and temperature sensor 492 are connected to processing device 170 and all are powered by power source 180. In this embodiment, processing device 170 is also connected to port 490. Port 490 may be, for example, a USB port to connect the system to a computer, smart-phone, or similar device. A wireless connection (e.g. a BLUETOOTH®) may also be used.

Typically, when hydrogen peroxide is introduced to cleaning case 110 containing catalyst 118, a chemical reaction occurs in which the catalyst chemically reduces, and thereby consumes, the peroxide. Complete consumption of the peroxide is recommended before inserting a lens into the eye, since ever trace amounts of peroxide can be very painful to the eye. Heat is generated during this chemical reaction. The rate and degree of temperature increase during the reaction and decrease after the reaction can be measured and will be a function of the amount of peroxide in the solution and the amount of available catalyst since catalyst material, typically a metal such as platinum, is also oxidized during the reaction. Thus, in one embodiment, changes in the temperature or temperature profile (i.e. the shape of a temperature vs. time curve) of the cleaning solution can be correlated to changes in the quality of the cleaning solution (e.g. amount of peroxide present) or the catalyst (how much catalyst is still available). A processing device can then be programmed to compare the temperature or temperature profile with a preset value. Thus, different messages can be displayed on the display device depending on whether the temperature sensor measures a temperature profile that falls within or outside of the acceptable temperature profile range.

Figure 5:
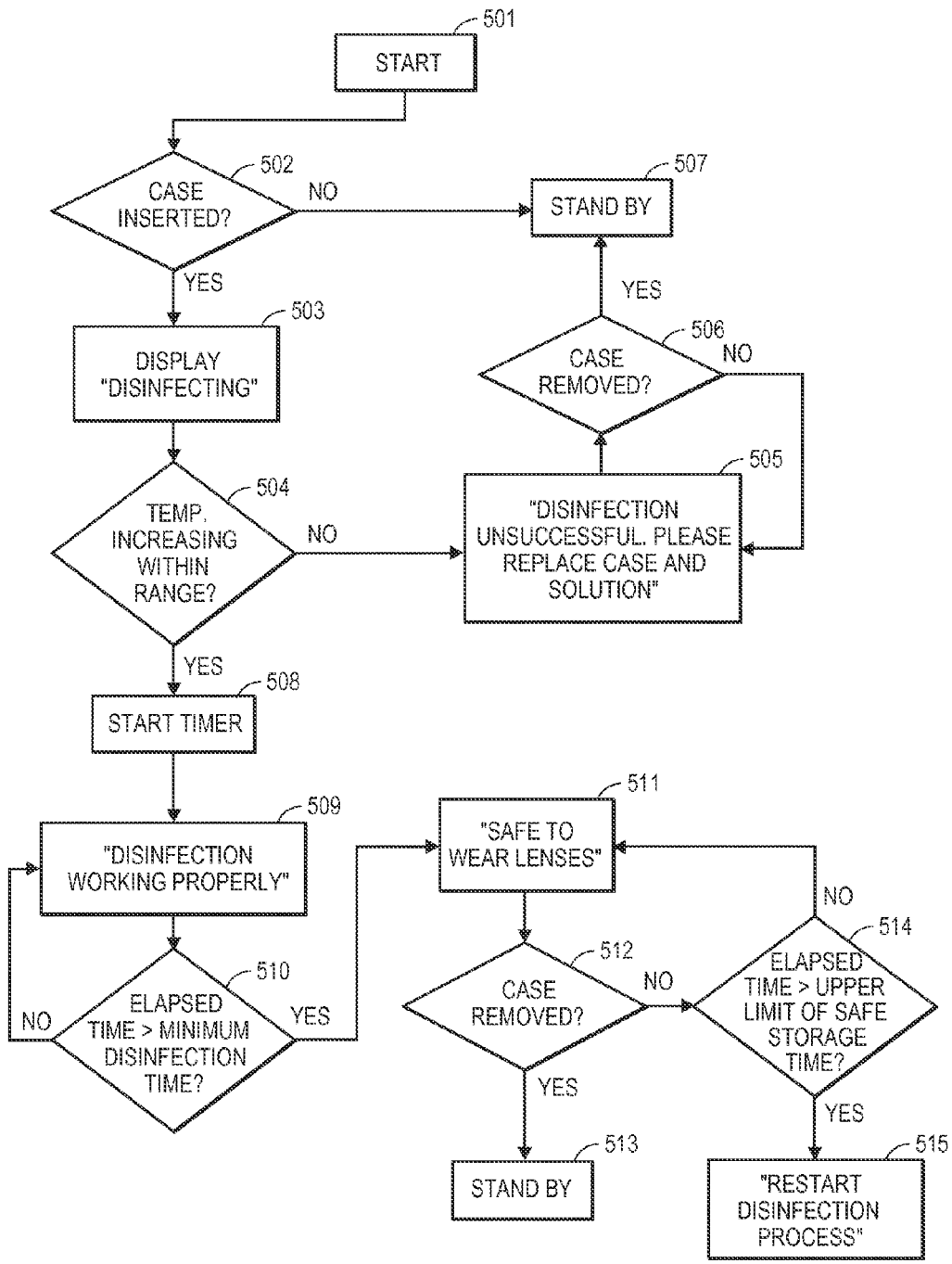
FIG. 5 illustrates another exemplary operational flowchart.

Referring to FIG. 5, various aspects of operation of certain embodiments of a contact lens storage system are shown. The process begins at step 501 after contact lenses and cleaning solution are placed in a cleaning case (e.g. cleaning case 110, FIG. 4B). At this time, the cleaning case should be inserted in the base unit. A trigger (e.g. trigger 460, FIG. 4B) and the processing device to which it is connected can be used to determine if the contact lens case has been placed into the base unit at step 502. If a cleaning case has been placed therein, a message such as "Disinfecting" can be displayed on a display panel (e.g. display panel 154, FIG. 4A) at step 503. If no cleaning case has been placed in the base unit, the display panel can display a message such as "Standing By" at step 507 and the base unit can be said to be in "standby mode". After the trigger has been tripped, the temperature profile of the solution in the cleaning case can be measured to determine if it falls within an acceptable temperature profile range at step 504. If "No" then a message such as "Disinfection unsuccessful. Please replace case and solution." can be displayed at step 505, after which the case can be removed at step 506 and the "Standing By" message can be displayed at step 507. If the temperature is found to be increasing within an acceptable range, then a timer can begin counting to a preset minimum disinfection time ("MDT") time for normal disinfection of a pair of contact lenses at step 508. At this time, a "Disinfection working properly" message can be displayed. This message can remain displayed as long as the elapsed time is not greater than the minimum disinfection time at step 510. Once the elapsed time ("ET") equals the minimum disinfection time at step 510, a "Safe to Wear Lenses" or "Disinfection Complete" message may be displayed at step 511. For example, the minimum disinfection time can be set at 6 hours. Other minimum disinfection times can be set according to such factors as how long it takes to measure the temperature profile, the size and shape of the lens case and catalyst, and the recommended minimum time of disinfection specified by the cleaning system (e.g., CLEAR CARE®, etc.). If the case is then removed at step 512, the base unit is returned to standby mode. If the case is not removed at step 512, then the timer continues to count. When the elapsed time measured by the timer reaches a preset upper limit of safe storage time ("SST") at step 514, a message such as "Please restart the disinfection process" can be displayed at step 515; if not, the "Safe to Wear Lenses" message can remain displayed. For example, the upper limit of SST may be about 18 hours, about 24 hours, about 7 days, or another time depending on the cleaning system used. Since after this time the risk of re-infection may increase, it may be advisable to remove the lenses from the cleaning case before this time. As will be appreciated by persons having ordinary skill in the art, the processing device, which can include one or more memory units, can store the values such as the elapsed time, the safe storage time, etc. and can perform the above-described comparisons and calculations.

Figure 6A:
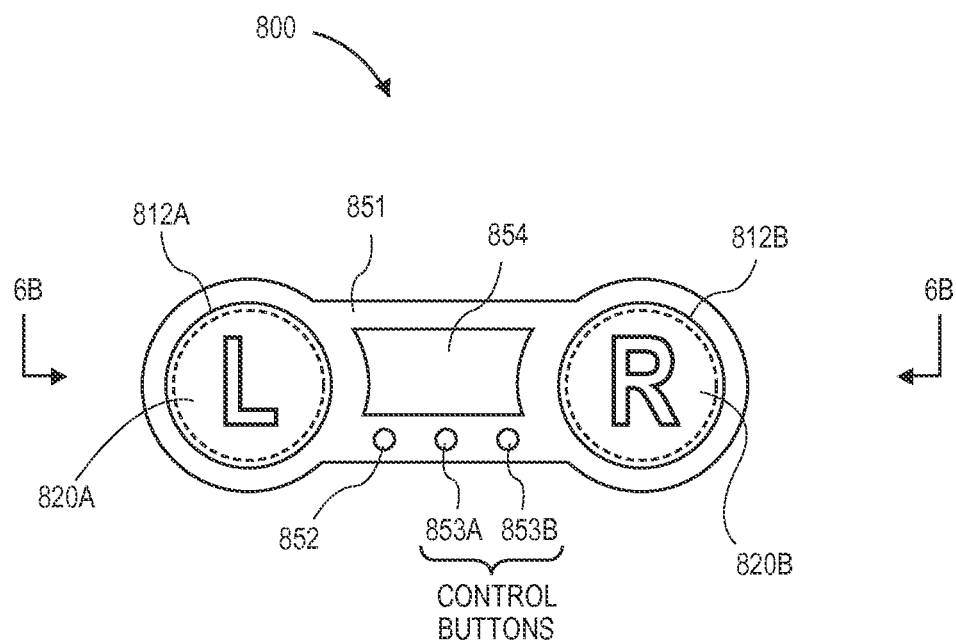
FIGS. 6A-6B illustrate a top view and a side view, respectively, of another contact lens storage system.
Figure 6B:
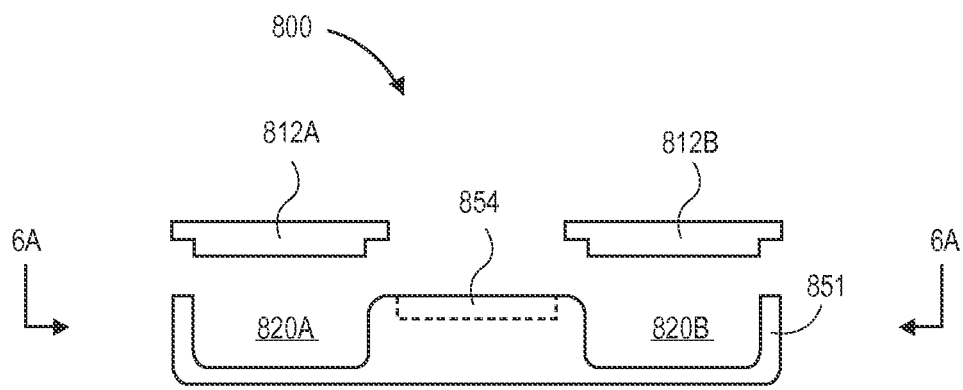

Referring to FIGS. 6A-B, an embodiment where the caddy itself receives the cleaning solution (i.e. where there is no separate cleaning case) is shown. Referring to FIG. 6A, caddy 800 in side view is shown, including caddy case 851, made of plastic or some other suitable material, indicator 852, control buttons 853A and 853B, display 854, reservoirs 820A and 820B, and caps 812A and 812B, which may be reversibly affixed (e.g. by screwing, snapping, form-fitting, friction fitting, etc.) to caddy case 851. Certain of these components are shown in side view in FIG. 6B. This caddy may include features illustrated in the other embodiments, and not explicitly shown here, such as a trigger, a timer, a processing device or a power source. The caddy shown in FIGS. 6A-B may also include a reaction sensor such as a temperature sensor, an electronic sensor, a pressure sensor, a sound sensor, or a gas sensor. For example, caddy 800 may include a temperature sensor of the type shown in FIG. 4B, or a pressure sensor (e.g. in caps 812A-B) of the type shown in FIGS. 17-18. The caddy may also include buttons or tabs under a portion of where the caps are placed which are depressed when the caps have been reversibly affixed to the case. When depressed, a signal can then be sent to the processing device to begin a timer or display a message, similar to the trigger described above.

Figure 7:
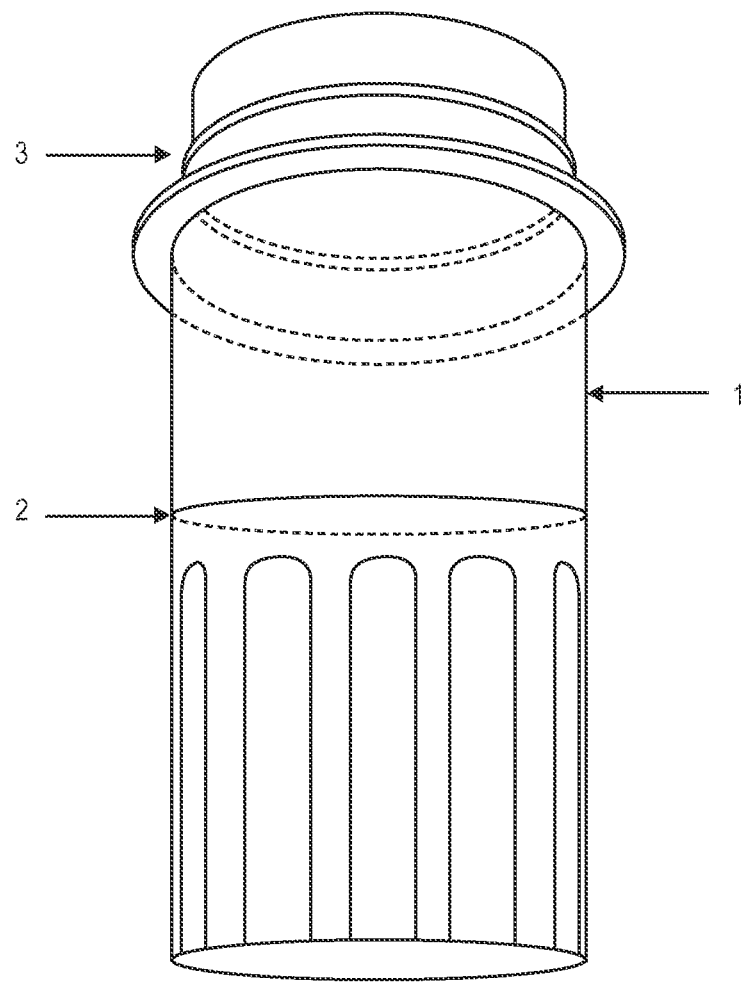
FIG. 7 illustrates a side perspective view of a contact lens cleaning case and monitor..

FIG. 7 illustrates a side perspective view of a contact lens cleaning case and monitor according to one embodiment of the invention. The embodiment of FIG. 7 has a contact lens cup 1 which is filled with buffered hydrogen peroxide solution to the fill line 2.

Figure 8A:
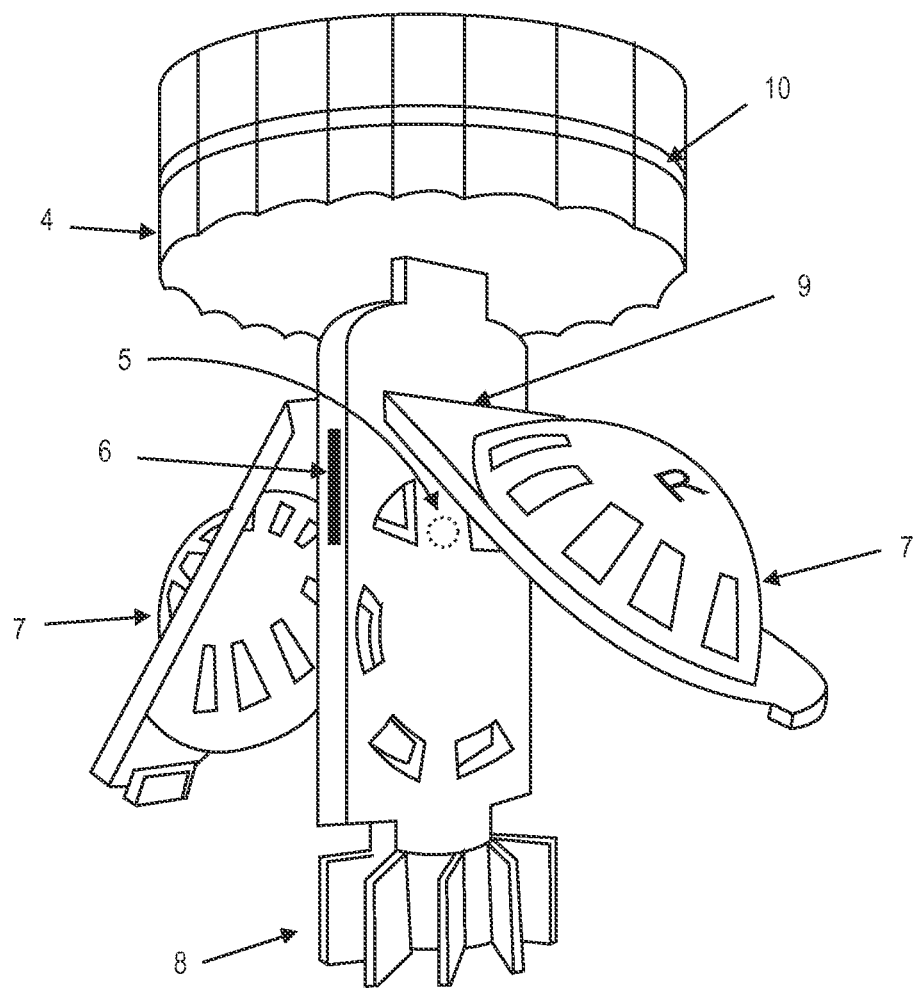
FIG. 8A illustrates a side view of the contact lens cap, lens basket, and platinum catalyst.

FIG. 8A illustrates a side view of the contact lens cap, lens basket, and platinum catalyst. The contact lens cup 1 uses a screw 3 to secure it to the screw cap 4 of FIG. 8A. The solution temperature sensor 5 monitors the temperature of the solution over time during the hydrogen neutralization process. In various embodiments, the solution temperature sensor 5 may be a thermistor or a thermocouple. Using a solution sensor 6, the microcontroller (not shown) senses that the contact lenses are immersed into the solution and initiates the monitoring process. The solution sensor 6 may include two electrodes, one of which is shown on the support beam of FIG. 8A. Solution sensor 6 may be located adjacent or near a top portion of lens basket 7 (not shown). The solution sensor may be a pair of conductivity electrodes. In various embodiments, when the presence of the solution is sensed using conductivity, the microcontroller 11 may supply power to one electrode and measures current at the other electrode. If current flows from one electrode to the other, the microcontroller determines the cap is placed into solution. The solution sensor may also be a capacitive sensor. In various embodiments, when the presence of the solution is sensed using capacitance sensors, the microcontroller may measure the capacitive load. An example of simple way to measure capacitance is through the use of an RC circuit, where the charging or discharging time of the effective capacitor is measured by the microcontroller; increased capacitance correlates with increased time. Examples of capacitive solution sensors can be found in U.S. Pat. Nos. 2,409,073, 5,145,323, and 5,238,369.

A pair of contact lens baskets 7 holds the contacts in place during the cleaning process. A platinum catalyst 8 neutralizes the hydrogen peroxide solution, which is an exothermic process. The basket hinge 9 allows the contact lens basket 7 to open, which allows the contacts to be attached or removed.

Figure 8B:
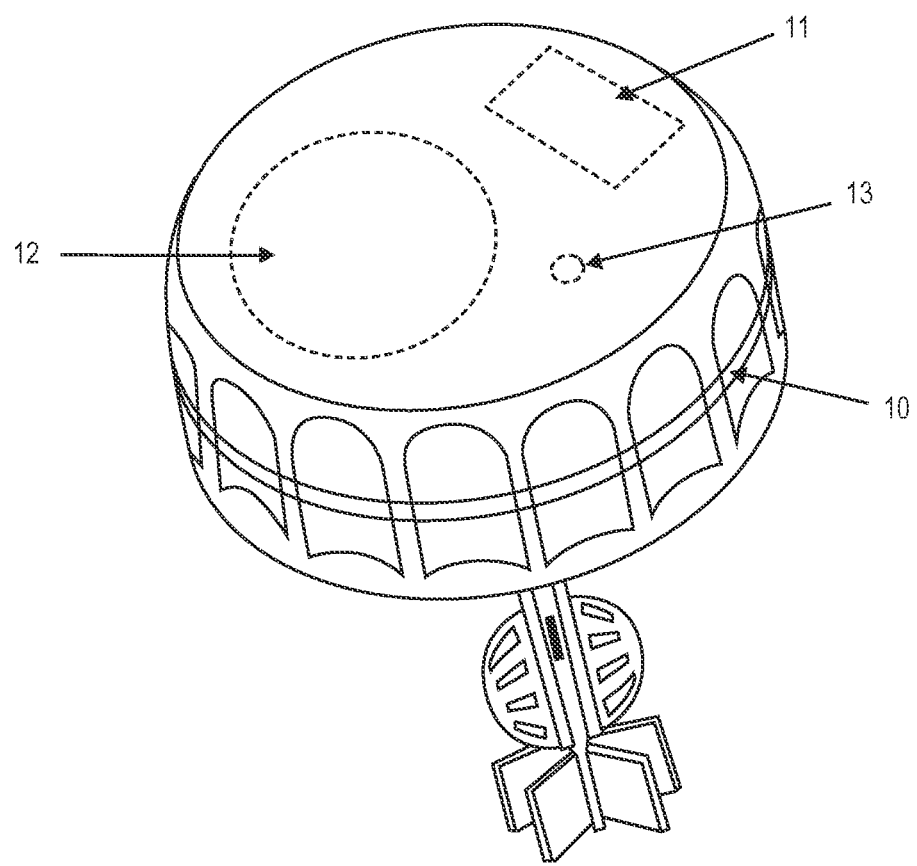
FIG. 8B illustrates a top perspective view of the contact lens cap showing the main internal components.

FIG. 8B illustrates a top view of the contact lens cap showing the main internal components. The main internal components of the contact lens cap may include a microcontroller 11, a reaction sensor such as an external temperature sensor 13, and a battery 12. The capacitive touch sensor 10 wakes the microcontroller 11 from low-power sleep mode. The capacitive touch sensor 10, commonly used in many hand-held devices such as cell phone capacitive touch screens, may communicate with the microcontroller 11 to identify hand touch. The microcontroller 11 may measure the capacitive load of the touch sensor 10. When a conductive object, such as a finger, gets in close proximity to a touch sensor, the capacitive load changes. Examples of touch sensors can be found in U.S. Pat. Nos. 4,186,392, 4,736,191, and 5,650,597. A battery 12 supplies power to the device.

Figure 13:
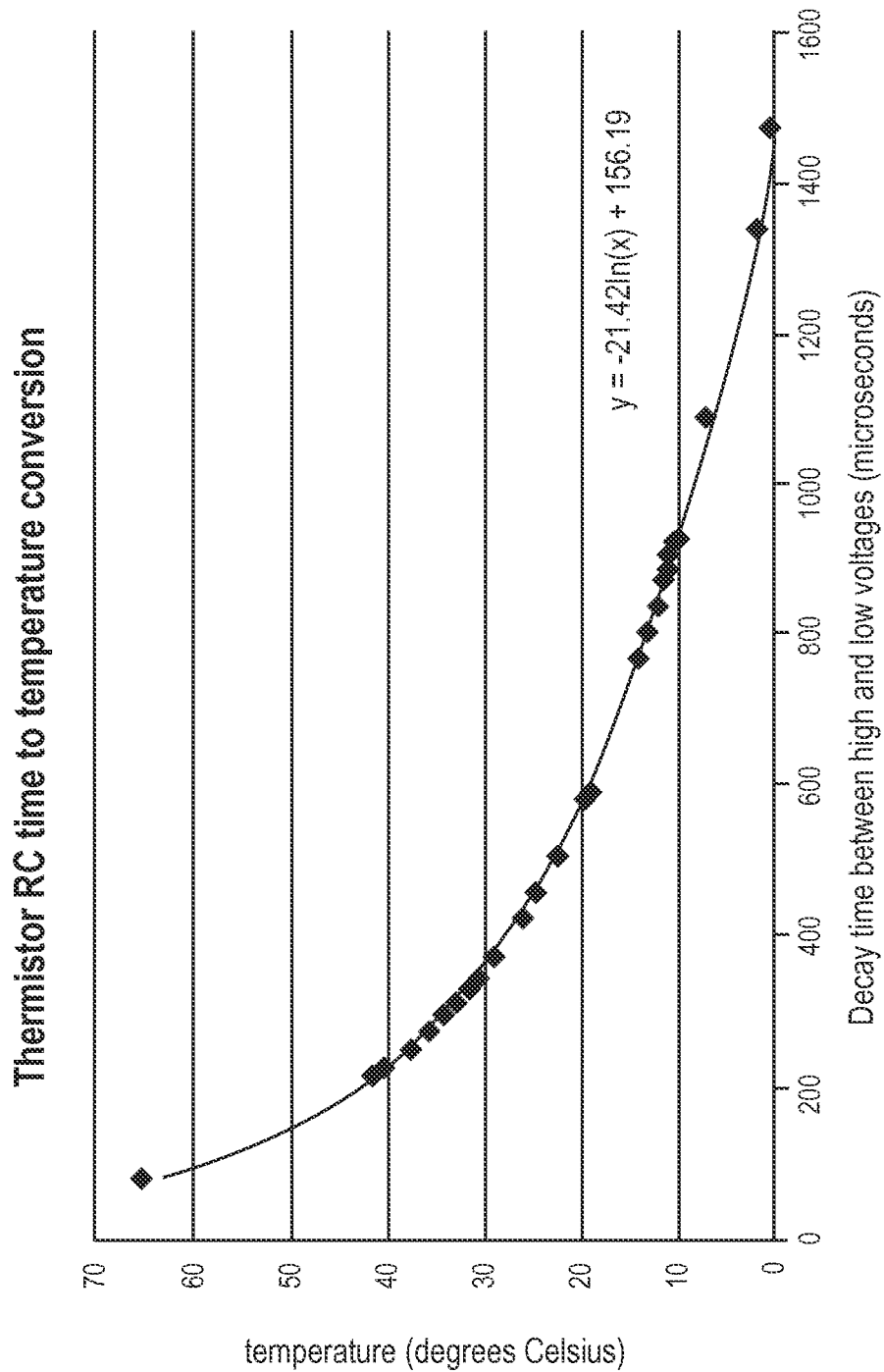
FIG. 13 illustrates an example of thermistor RC time to temperature conversion.

The external temperature sensor 13 measures the temperature of the air around the cup 1 and corrects for external heating or cooling of the solution. In various embodiments, the external temperature sensor 13 may be a thermistor or a thermocouple. An example how the microcontroller 11 may measure temperature through the use of a thermistor, is with the use of an RC circuit. The thermistor (for example a 33 k NTC-type), which has variable resistance with respect to temperature, may be connected in parallel with a capacitor of known, fixed capacitance (for example 1000 pF). The microcontroller initially charges the capacitor to a specific higher voltage (for example, approximately 4.5V). When the initial voltage is reached, the charging process is stopped, and time is measured for the thermistor to discharge the capacitor to a specific lower voltage (for example, approximately 1.4V). Since resistance of the thermistor is dependent on temperature, temperature can be easily calculated by the microcontroller 11 by time measurements between the higher and lower voltages. Measurement results from this example are illustrated in FIG. 13.

In one embodiment, the microcontroller 11 may measure temperature through the use of a thermocouple by measuring the current generated by the thermocouple, which is composed of two dissimilar thermoelectric characteristics. The current is converted to the digital signal, by an analog-to-digital converter, for the microcontroller to process. Since current is dependent on temperature, the microcontroller 11 can calculate the temperature based on this current. Examples of a thermocouple can be found in U.S. Pat. Nos. 2,985,949 and 4,588,307.

Figure 8C:
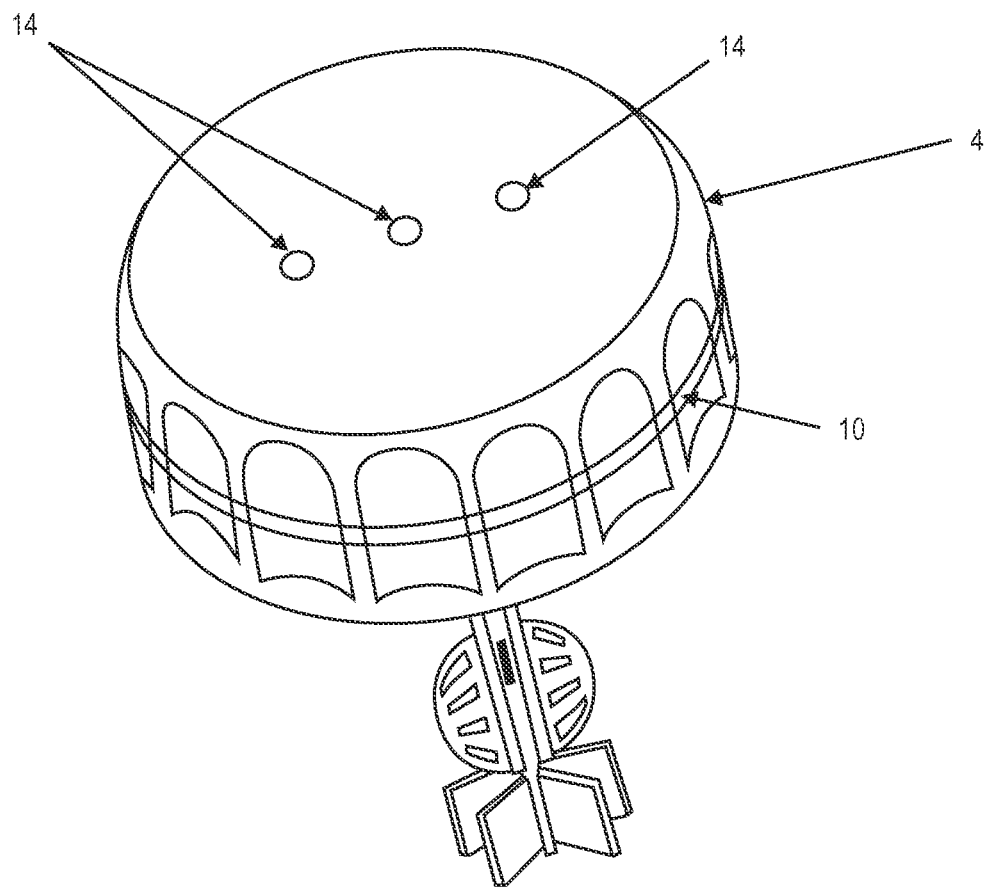
FIG. 8C illustrates another top perspective view of the contact lens cap showing an LED configuration.
Figure 8D:
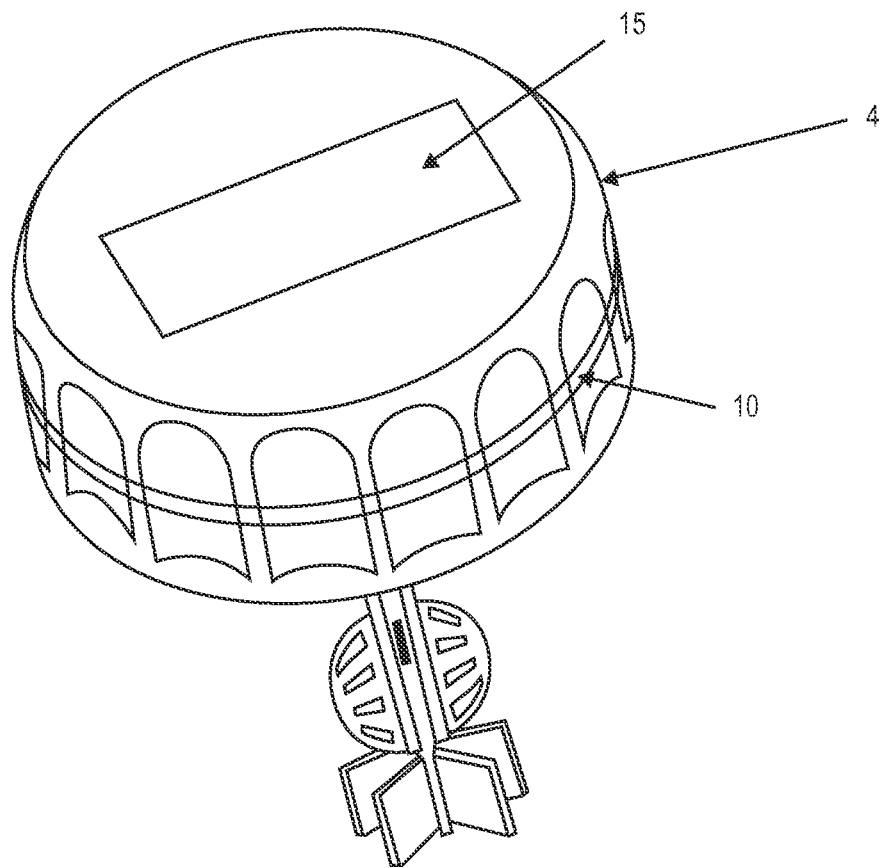
FIG. 8D illustrates another top perspective view of the contact lens cap showing a LCD configuration.

FIG. 8C illustrates a top view of the contact lens cap showing a display using an LED configuration. The LED colored light or lights 14 of FIG. 8C indicate(s) the status of the solution. FIG. 8D illustrates a top view of the contact lens cap showing a display using an LCD configuration. The optional LCD display 15 may supplement or replace the LED light or lights in communication of the status of the solution or device to the user. The status of the solution or device may include text which reads "analyzing the solution's cleaning process", "wait for solution to complete cleaning process", "safe to insert contacts into eye", "contacts unsafe to insert contacts into eye, redo cleaning process", "cleaning process not functioning properly, replace solution and/or case", and "battery low". The indications may be done by a colored LED light or lights such as for example red, yellow, orange, green, and short messages on the optional LCD display. The short messages may include "BATT", "WAIT", "OK", "REDO", "BAD", "USE", "SAFE", "LOW", "CLEANING", "ANALYZE", "REPLACE". In some embodiments, an indication may be provided as an audio signal.

EXAMPLE 1

Figure 9:
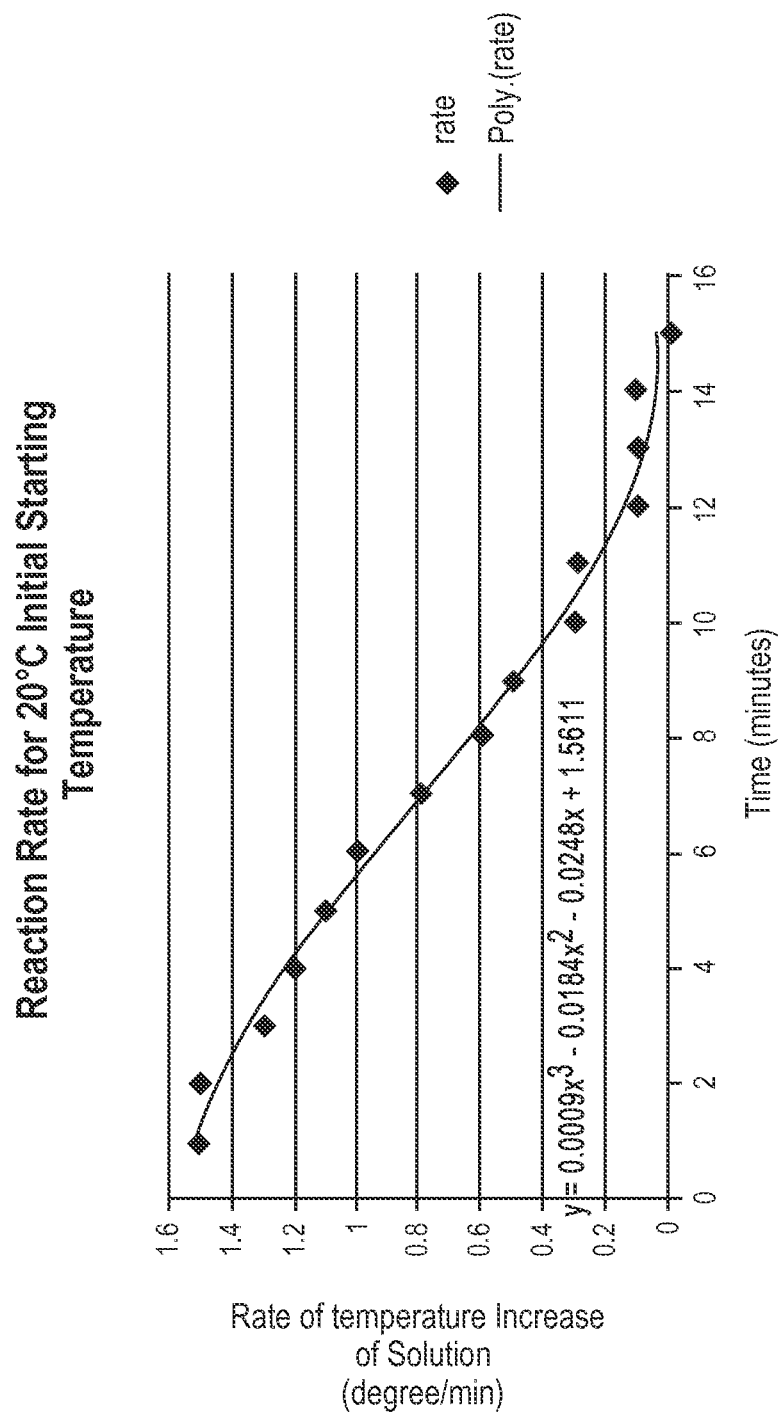
FIG. 9 illustrates the rate of temperature increase of solution over time.

The exothermic reaction monitored by the reaction sensor of this invention can be illustrated by this example. The contact lens case was a 20 mm diameter and a 2 mm thick plastic-walled reaction vessel such as the one shown in FIG. 7. The contact lens case was thermally insulated from the environment to negate external temperature influence. The case was filled with 10 ml of disinfection solution (a solution of 3% hydrogen peroxide, 0.85% sodium chloride, phosphonic acid, and phosphate buffer) at an initial temperature of 20.0° C. The contact lens cap contained a cogwheel-shaped, platinum catalyst disc (comparable to the common ~10.4 $cm^2$/1150 µg platinum catalyst currently commercially available and used in contact lens care). The thermal gradient was recorded over time with an imbedded thermocouple. For a 20° C. solution, the temperature initially increased at a rate of approximately 1.5° C. per minute. Since the solution's peroxide concentration decreases over time, the rate of temperature change (exothermic reaction) begins to slow. One competing event is that exothermic reactions accelerate with an increase in temperature. The resulting reproducible temperature profile is illustrated in FIG. 9, which can be predicted with the mathematical formula:

RATE (20° C.)=rate of temperature change without contribution from external air temperature influence, when the solution in at 20° C. (Celsius/minute).

The formula may also be expressed as:

RATE (20° C.)=(0.00009×$TIME^3$)−(0.0184×$TIME^2$)−(0.0248×TIME)+1.5611 where TIME is the reaction time (minutes).

Although the curve appears to be polynomial, linear approximation can also be used for simpler calculations:

RATE (20° C.)=(−0.124×TIME)+1.6725

Figure 10:
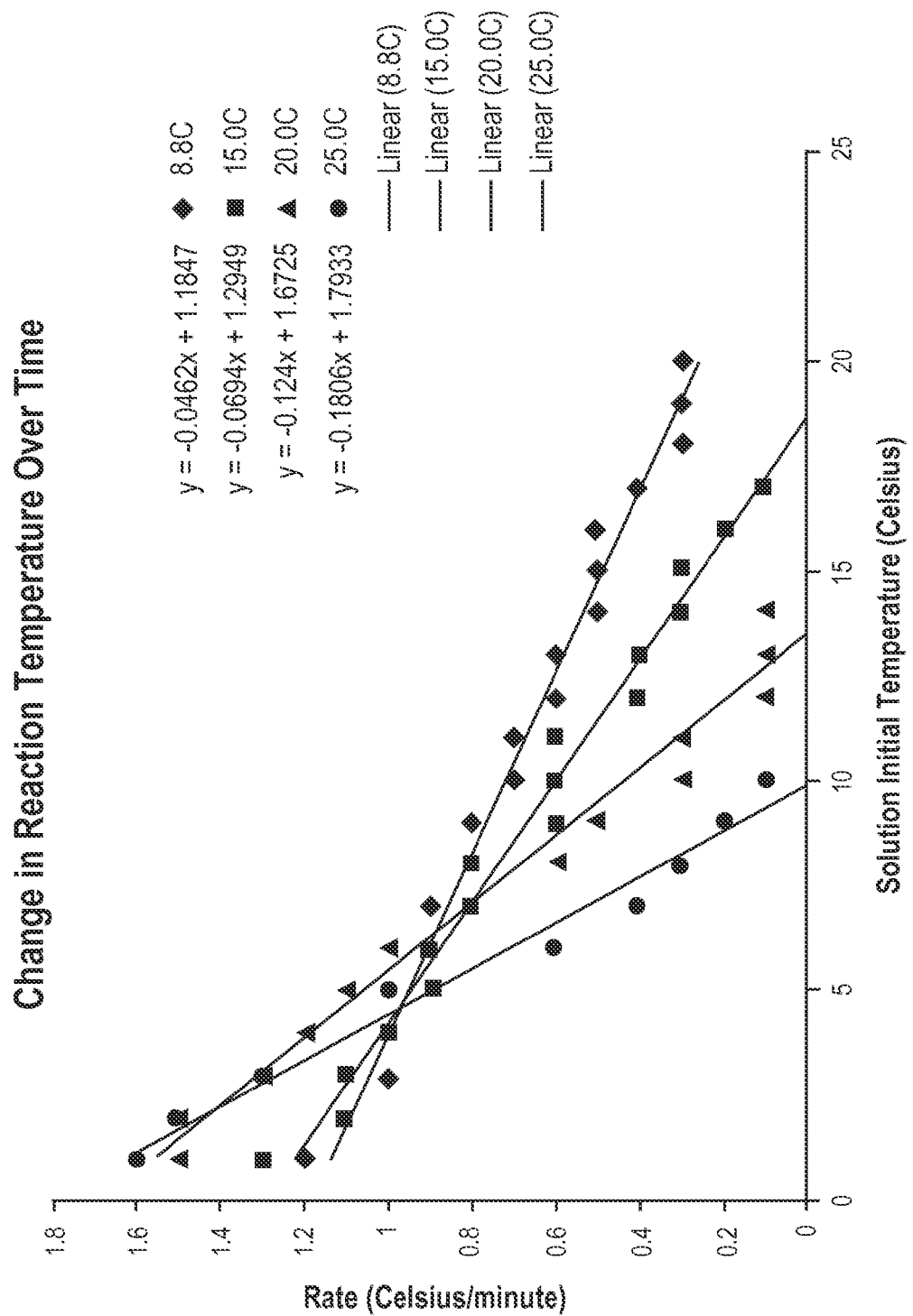
FIG. 10 illustrates the rate of dependence on initial solution temperatures.
Figure 11:
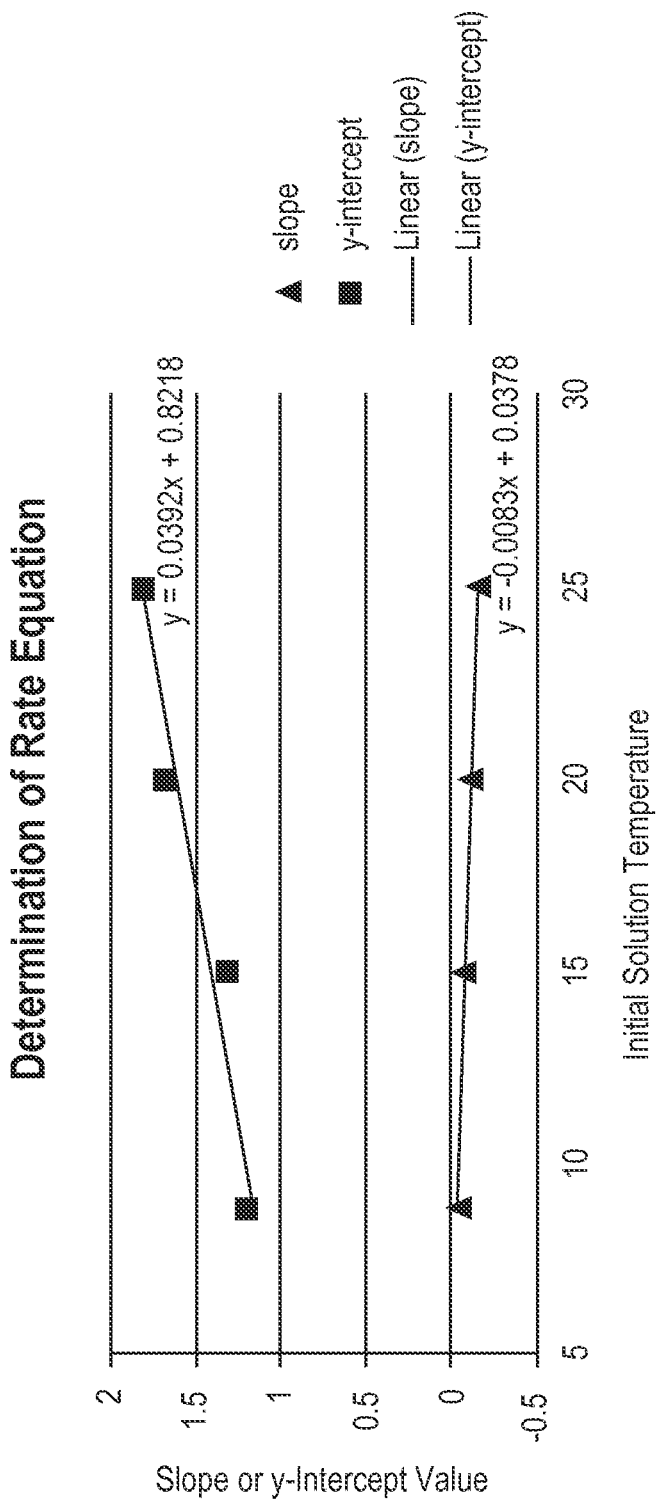
FIG. 11 illustrates the determination of equation of formula slope and y-intercept.

The experiment described above was repeated at different initial solution temperatures. FIG. 10 illustrates the reaction rate's dependence on initial solution temperatures. As shown in FIG. 10, the exothermic reaction is dependent on the initial temperature of the solution. A decrease in initial solution temperature has a decrease in rate of temperature change over time, while an increase in temperature has an accelerated rate of temperature change over time. FIG. 11 illustrates the determination of equation of formula slope and y-intercept. As shown in FIG. 11, the slope and y-intercept of these graphs are fairly linear with respect to initial solution temperature. Thus, a simple mathematical calculation can be used to predict the temperature rate of change at any time point for a given initial solution temperature.

RATE (1)=rate of temperature change without contribution from external air temperature influence (Celsius/minute).

The formula may also be expressed as:

$$\text{RATE (1)} = (((-0.008 \times IST) + 0.037) \times \text{TIME}) + ((0.039 \times IST) + 0.821)$$

Where IST is the initial solution temperature (Celsius) and TIME is the reaction time (minutes).

Figure 12:
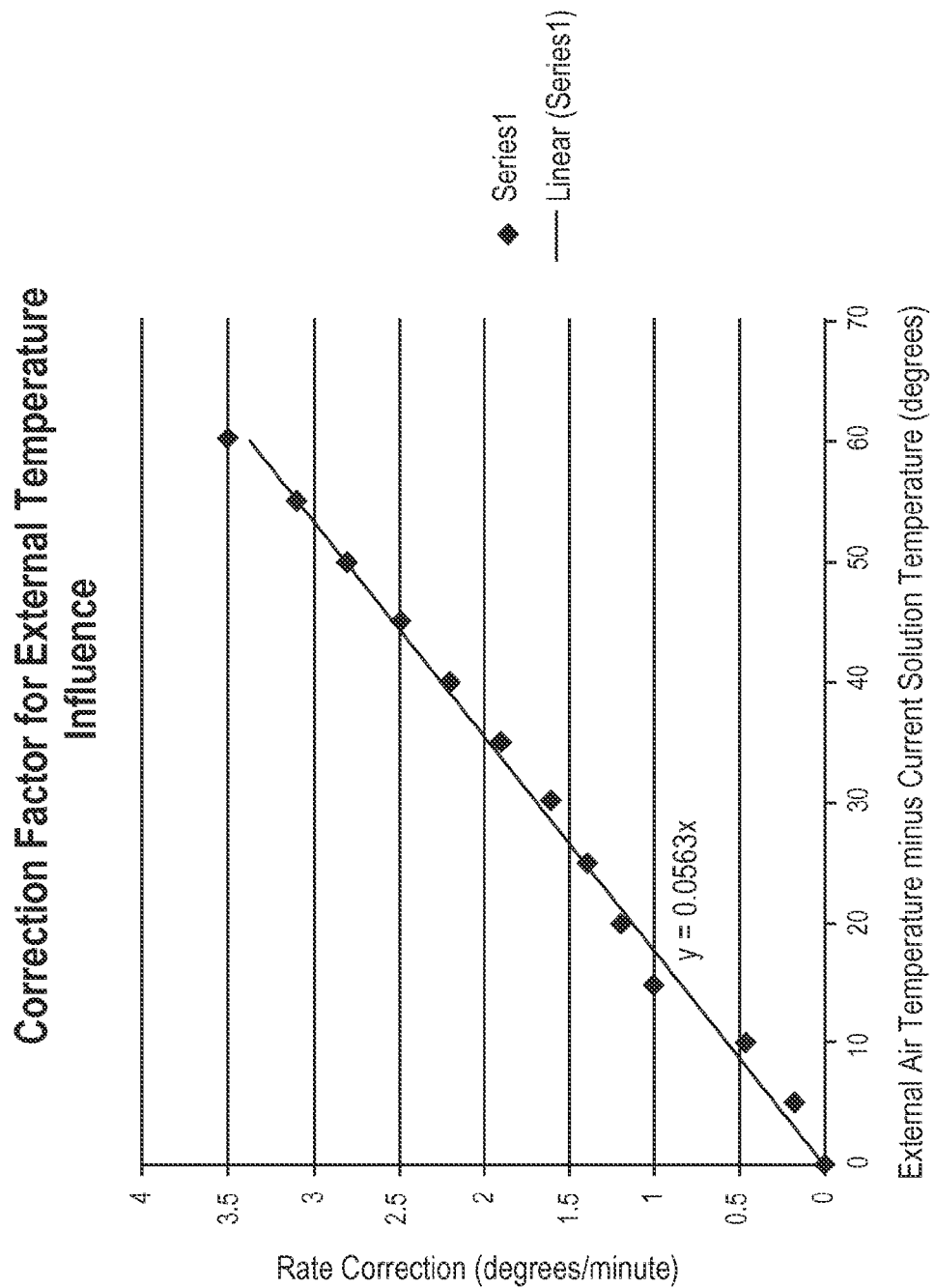
FIG. 12 illustrates the determination of rate in which air heats the solution inside contact lens case.

Since the mathematical calculation does not account for the external air temperature warming the contact lens case, one can easily correct for this. The experiment described above was performed at multiple ambient air temperatures. FIG. 12 illustrates the determination of the effect of ambient air temperatures on the heat of the solution inside contact lens case during the exothermic disinfection process. The effect was found to be linear with respect to the instantaneous temperature difference between the air temperature and solution temperature. The cooling effect also fits this equation, where the air temperature was lower than the solution temperature, although a negative value. Thus, the overall rate is:

RATE (2) = rate of change of solution temperature without contribution from the exothermic neutralization reaction (Celsius/minute) (rate that air heats solution)

The formula may be expressed as:

$$\text{RATE}(2) = 0.056 \times (CET - CST)$$

Where CST is the current solution temperature (Celsius) and CET is the current external temperature (Celsius).

The THERORETICAL RATE may then be calculated as the overall rate of change of solution temperature. The theoretical rate may be expressed as:

$$\text{THERORETICAL RATE} = \text{RATE}(1) + \text{RATE}(2)$$

$$\text{THERORETICAL RATE} = (-0.008 \times IST + 0.037) \times \text{TIME} + (0.039 \times IST + 0.821) + 0.056 \times (CET - CST)$$

This equation only fits a specific contact case design, solution formulation, peroxide concentration, and catalyst design and quality. This is advantageous, since an abnormally high or low peroxide concentration and/or a reduction in quality of the platinum catalyst can be easily identified by a comparison of theoretical and actual temperature measurements.

A method for using the device may begin when a user places contact lenses into the contact lens baskets 7 of the contact lens cap 4, and closes the baskets 7. The contact lens case cup (reaction vessel) 1 is filled with hydrogen peroxide disinfection/cleaning solution up to the fill line 2. The contact lens cap 4 is grasped by the user's hand. The user's hand is sensed by the capacitive touch sensor 10, which wakes the microcontroller 11 from low-power mode. The microcontroller 11 then monitors the solution sensor 6 to sense when the contacts lenses are immersed in to the solution. For purposes of discussion, conductivity electrodes are used as an example of the solution sensor. The exemplary solution sensor is not intended to be limiting. The microcontroller 11 may sense when the contact lenses are immersed because the solution contains ions which allow electricity to flow from one electrode to the other. Since the conductivity electrodes 6 are located near or above the solution temperature sensor 5, contact lenses, and fill line 2, there is confirmation that there is sufficient solution added to the contact lens case cup (reaction vessel) 1. The conductivity electrodes 6 signal the microcontroller 11 to initiate the monitoring of the contact lens solution and to start the reaction timer. For example, the microcontroller 11 may cause a yellow LED light 14 to blink rapidly or a display to provide the message "ANALYZE" on the LCD display 15. The microcontroller 11 would then take an initial solution temperature measurement (IST). In various embodiments, the microcontroller 11 may take a solution temperature measurement with a solution thermistor or thermocouple 5 at 1.5 minutes and 0.5 minutes and take the difference of these two numbers (ACTUAL RATE); the microcontroller 11 will also take a measurements at 1.0 minute (TIME=1.0) with solution thermistor or thermocouple 5 (CST), and a measurement with external temperature sensor 13 (CET). The values may be used in the following example equation:

$$\text{THEORETICAL RATE} = (-0.008 \times IST + 0.037) \times \text{TIME} + (0.039 \times IST + 0.821) + 0.056 \times (CET - CST)$$

For example, if the ACTUAL RATE is within +/−20% of the THEORETICAL RATE, the device identifies that the solution and platinum catalyst are performing as expected; the device may then slowly blink a yellow LED light 14 or display "CLEANING" on the LCD display 15. For example, if the ACTUAL RATE is not within +/−20% of the THEORETICAL RATE, the device identifies that the solution and platinum catalyst are not performing as expected; the device may blink a red LED light 14 or display "REDO" or "BAD" on the LCD display 15.

If the device identified that the solution and platinum catalyst are performing as expected, a specific time will be allowed to elapse which is appropriate for the complete neutralization of the hydrogen peroxide at the given solution temperature (approximately 6 hours at 20° C.). At this point, the contacts are considered ready to wear, and the device may then slowly blink a green LED light 14 or display "USE" or "SAFE" or "WEAR" on the LCD display 15. If the conductivity electrodes 6 and capacitive touch sensor 10 do not sense that the screw cap 4 was removed from the contact lens cup 1 which contains the neutralized solution, the device may then slowly blink a green LED light 14 up to the point where the contact lens are not longer safe to place into the eye at the given solution temperature (approximately 7 days at 20° C.). At this point, the device may then slowly blink a red LED light 14 or display "REDO" on the LCD display 15.

The device may also count the number of times the cleaning process was preformed, and blink a red LED light 14 or display "BAD" or "REPLACE" on the LCD display 15 after the maximum number of uses was exceeded. An audio indication may also be provided to indicate the maximum number of uses was exceeded. The device may also count the number of days that have elapsed after the initial use, and blink a red LED light 14 or display "BAD" or "REPLACE" on the LCD display 15 after the maximum number of days was exceeded.

Figure 14:
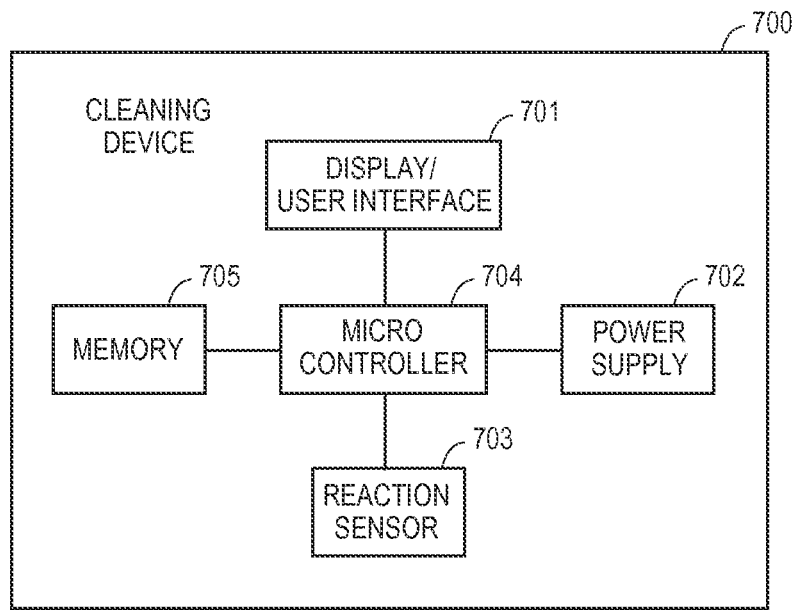
FIG. 14 illustrates a block diagram of a cleaning device for a medical device.

FIG. 14 illustrates a block diagram of a cleaning device 700 for a medical device. Cleaning device 700 has a microcontroller 704 that is powered by the power supply 702. The microcontroller 704 controls and communicates with the display/user interface 701, reaction sensor 703, and memory 705. The device's operation program and user data is stored on the memory 705, and the information is accessed on demand by the microcontroller 704. The microcontroller's program may be initiated by a signal from the reaction sensor 703 or from a signal from the user, via the display/user interface 701, such as a display touch screen. The microcontroller 704 takes readings from the sensor over time, makes calculations with the measurements and the data stored in the memory, and displays a result on the display/user interface 701.

Figure 15:
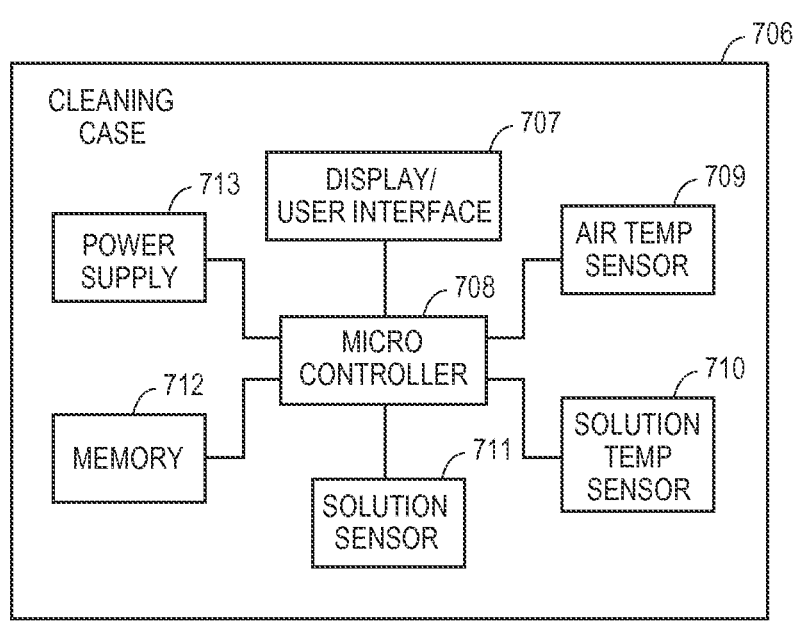
FIG. 15 illustrates a block diagram of an exemplary temperature sensing contact lens cleaning case.

FIG. 15 illustrates a block diagram of an exemplary temperature sensing contact lens cleaning case 706. The cleaning case 706 has a microcontroller 708 that is powered by the power supply 713. The microcontroller 708 monitors the solution sensor 711 to sense when solution is present. When the microcontroller 708 determines that solution is present, readings from air temperature sensor 709 and solution temperature sensor 710 are obtained. These readings, combined with calibration data stored in the memory 712, are converted to temperature measurements by the microcontroller 708. The microcontroller 708 then stores these historical temperature measurements in the memory 712 for later retrieval. After a specific duration, the temperature measurements are recalled from the memory 712 by the microcontroller 708. The microcontroller 708 determines what signals should be sent to display 707.

Figure 16A:
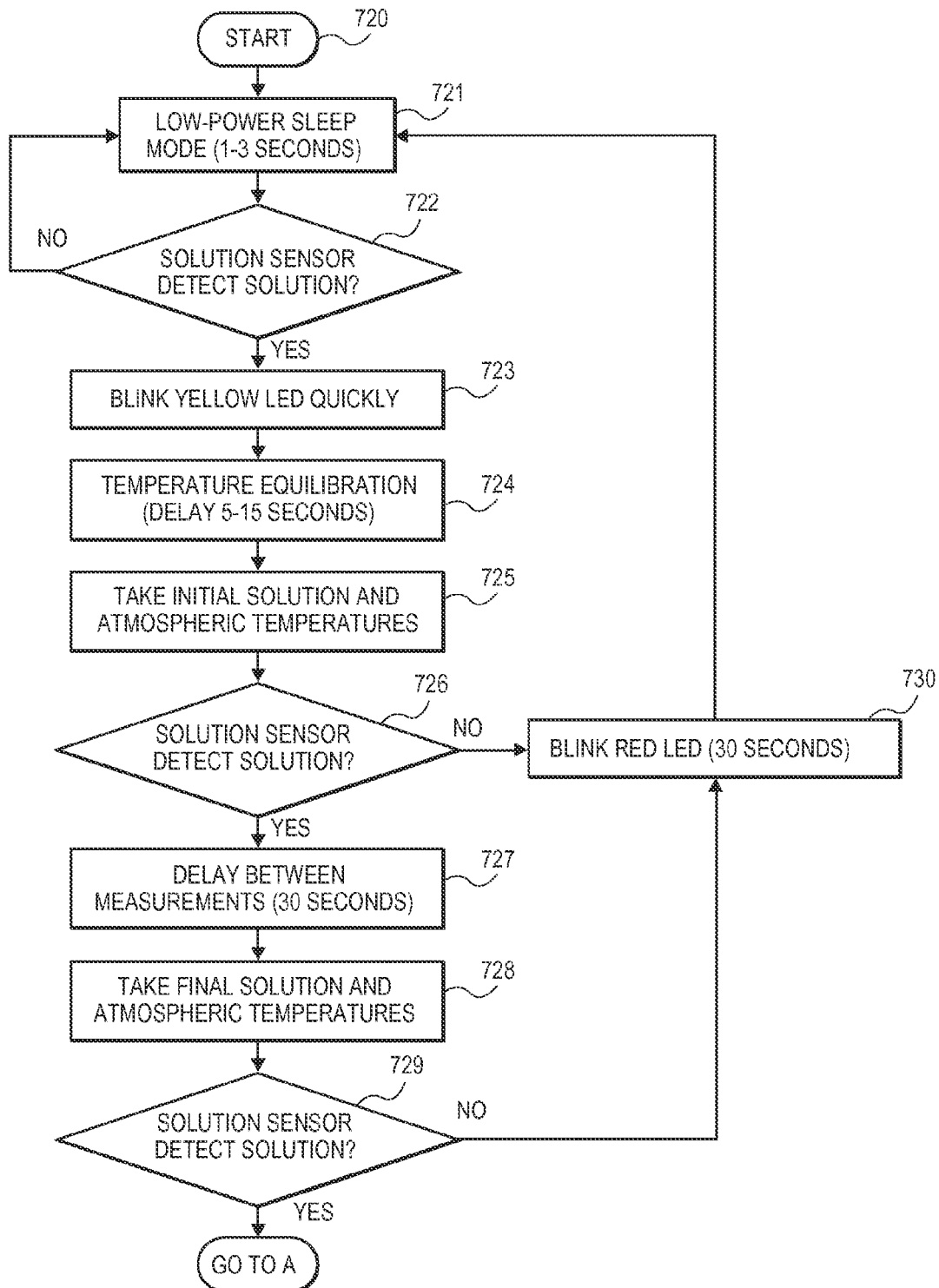
FIGS. 16A-16B illustrates another exemplary operational flowchart.
Figure 16B:
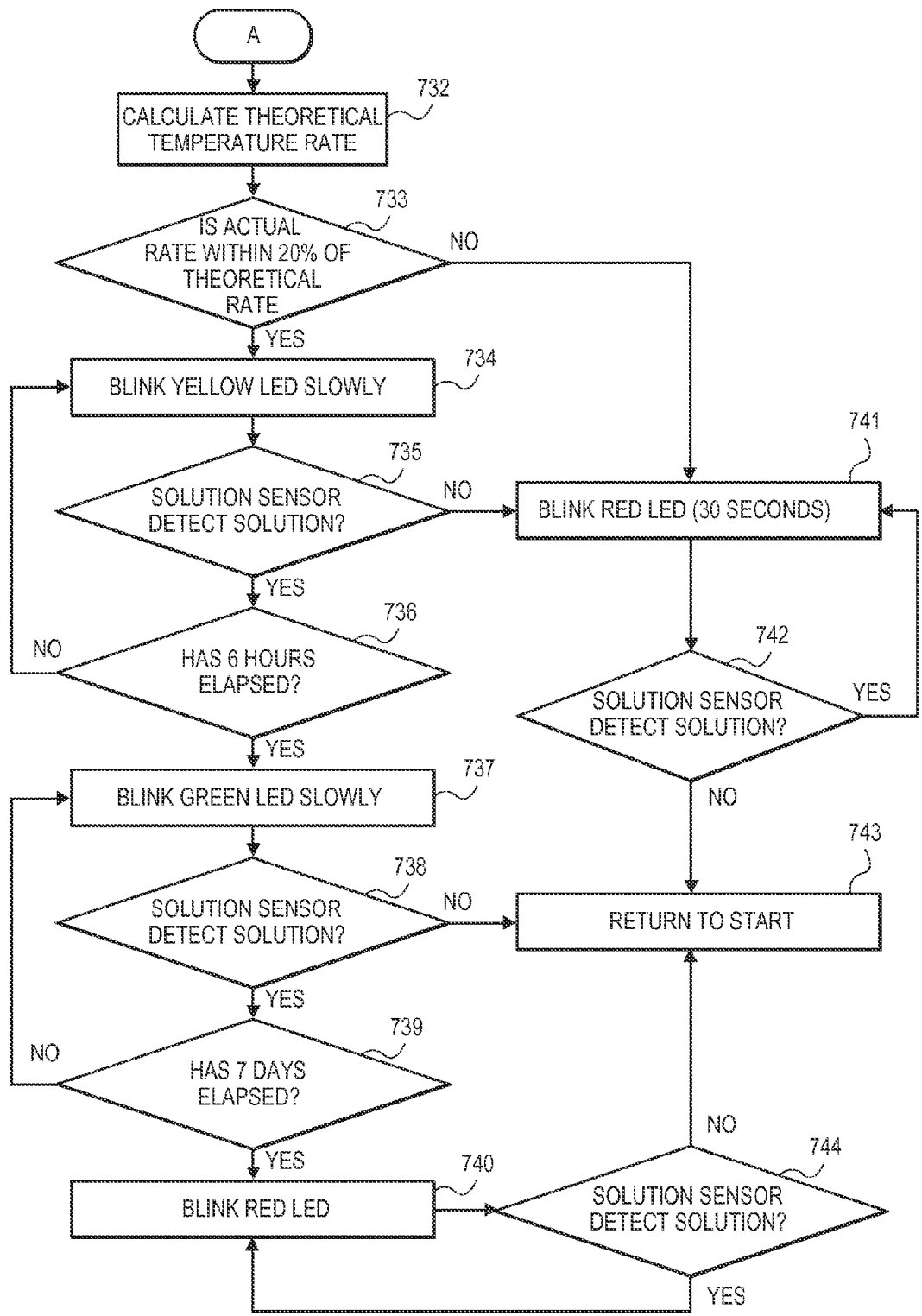

FIGS. 16A-B illustrate an example of an operational flow chart for using a three light LED display configuration. The flow of operation described herein is for illustrative purposes and is not intended to be limiting. In various embodiments, the process begins at step 720 when the cleaning case (e.g. cleaning vial FIG. 7 and cap FIG. 8A) is powered on. In some embodiments, the device is normally in low-power sleep mode at step 721 to preserve limited battery life. The device may wake up from low-power sleep mode every 1 to 3 seconds for a period of a few microseconds to sense if cleaning solution has been added to the device at step 722. If no solution is detected, the device goes back into sleep mode. If solution is detected, the device blinks the yellow LED quickly at step 723. For example, the device LED may blink twice per second. Quick blinking may indicate the device is determining if the cleaning solution and system are functioning properly. The device delays 5 to 15 seconds before taking a baseline temperature measurement at step 724, to allow for temperature equilibration of the cleaning solution, vial, and cap. After equilibration, initial solution and atmospheric temperature measurements are taken at step 725. The solution temperature is used as a reference point, in which future solution temperature rates can be determined. Since the cleaning solution can either be heated by the exothermic chemical reaction or the heat from the environment, it is useful to take atmospheric temperature measurements. Once the air temperature is known, atmospheric heating of the solution can be factored out, thereby giving a more accurate measurement of chemical heating. The device routinely detects if the cap is continuously immersed in solution at step 726.

If no solution is detected at step 726, the LED will blink red at step 730, indicating that the cleaning process has been interrupted and that it is unsafe to place the contact lenses into the eye. The red blinking LED continues to blink for 30 seconds, followed by return to low-power sleep mode at the start of the sequence. If solution is detected, the microcontroller delays for 30 seconds at step 727. Solution and atmospheric temperature measurements are re-sampled or taken at step 728. The device routinely detects if the cap is continuously immersed in solution at step 729, and the process proceeds if solution is detected. Theoretical temperature rate is calculated at step 732 from the solution temperature measurements and corrected by the atmospheric temperature measurements. If the actual temperature rate is not within 20% of the calculated theoretical temperature rate at step 733, then the LED blinks red to indicate that the lenses are not safe to insert into the eye at step 741. After 30 seconds, the device may continue to wait until no solution is detected at step 742, and then the process returns to start at step 743.

If the actual temperature rate is within 20% of the calculated theoretical temperature rate at step 733, then the device blinks the yellow LED slowly at step 734, for example once per 2 to 3 seconds. The purpose of the slowly blinking is to indicate that the device has determined that the cleaning solution and system are functioning properly, and the device is cleaning the contact lenses. The device detects if the cap is continuously immersed in solution at step 735. If solution is detected, the device proceeds to allow 6 hours for the cleaning solution to complete the cleaning/neutralization cycle at step 736. If 6 hours has elapsed, the device blinks the green LED slowly at step 737, which indicates to the user that the device has finished the cleaning /neutralization cycle, and the contact lenses are safe to insert into the eye. The device continues to blink the green LED until no solution is detected at step 738, where it returns to the start at step 743. If solution is continued to be detected at step 738, and 7 days has elapsed at step 739, then the LED blinks red at step 740 to indicate that it is no longer safe to insert the contact lenses into the eye. This is due to a possibility that microbes may have re-infected the sterile solution. The red LED will continue to blink until no solution is detected at step 744.

Figure 17:
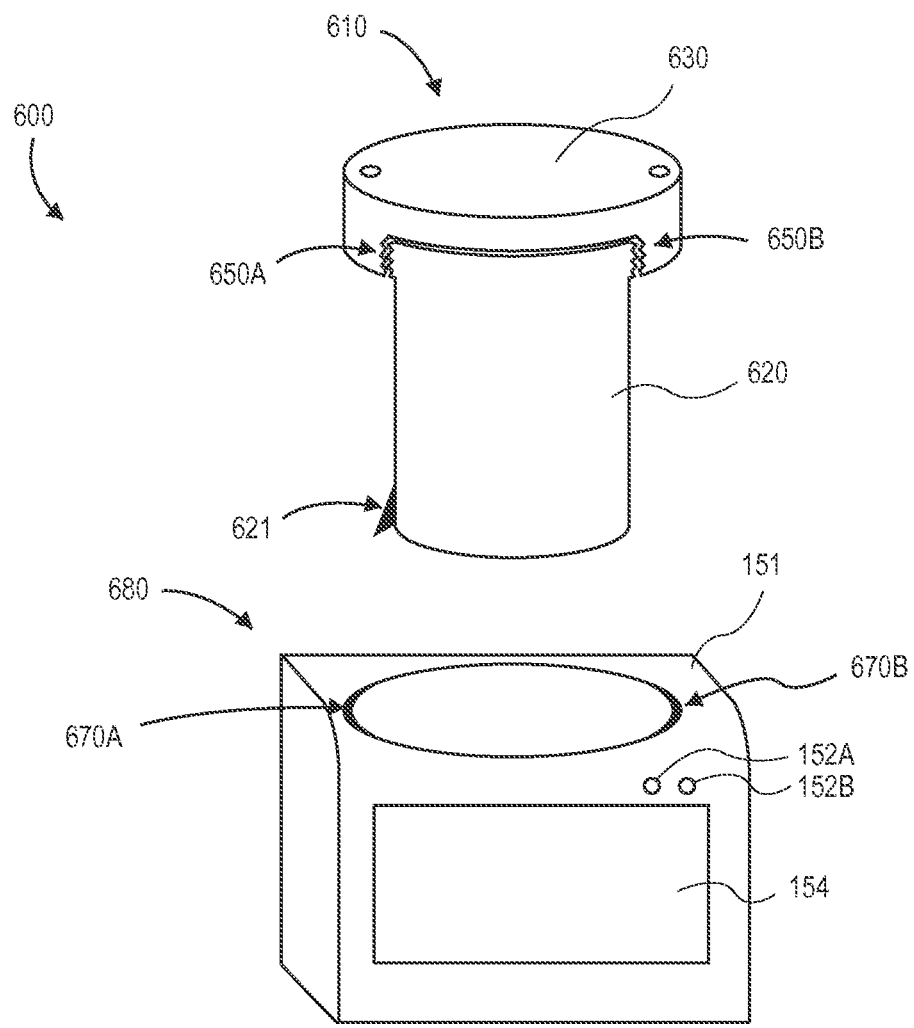
FIG. 17 illustrates another exemplary contact lens storage system.

FIG. 17 illustrates an embodiment of a system 600 comprising a cleaning case 610 and a caddy 680, in which pressure in the headspace above the cleaning solution is measured within the cleaning case, and messages based on the pressure profile are displayed on the caddy. Cleaning case 610 includes cap 630 and may also include aforementioned components, not shown here, such as a basket for holding contact lenses, a catalyst, and others. In this embodiment, cap 630 includes case contacts 650A and 650B. Also shown is caddy 680, which includes features described above such as caddy case 151, indicators 152A and 152B, and display panel 154. Also shown are caddy contacts 670A and 670B.

Still referring to FIG. 17, case contacts 650A and 650B make electrical contact with caddy contacts 670A and 670B when the case is placed in caddy 680. In this way there is an electrical communication between the case and the caddy to enable other features of this system. Cleaning case 610 also includes cylinder 620, which may have an orienting component for rotationally positioning the cleaning case once it is placed in the caddy such that case contacts 650A and 650B make proper contact to caddy contacts 670A and 670B. Such orienting component may be a fin, such as fin 621 shown, or may be a groove, bump, dimple, or similar structure. In such case, the caddy will also include a corresponding receiver, not shown, which can receive or mate with the structure on the cylinder. Such receiver can be a groove, fin, dimple or notch, and is not shown in the figure. For example, caddy 680 can include a groove to receive fin 621 when case 610 is placed in the caddy. Other mechanisms for properly orienting the case in the caddy may be easily envisaged.

Figure 18A:
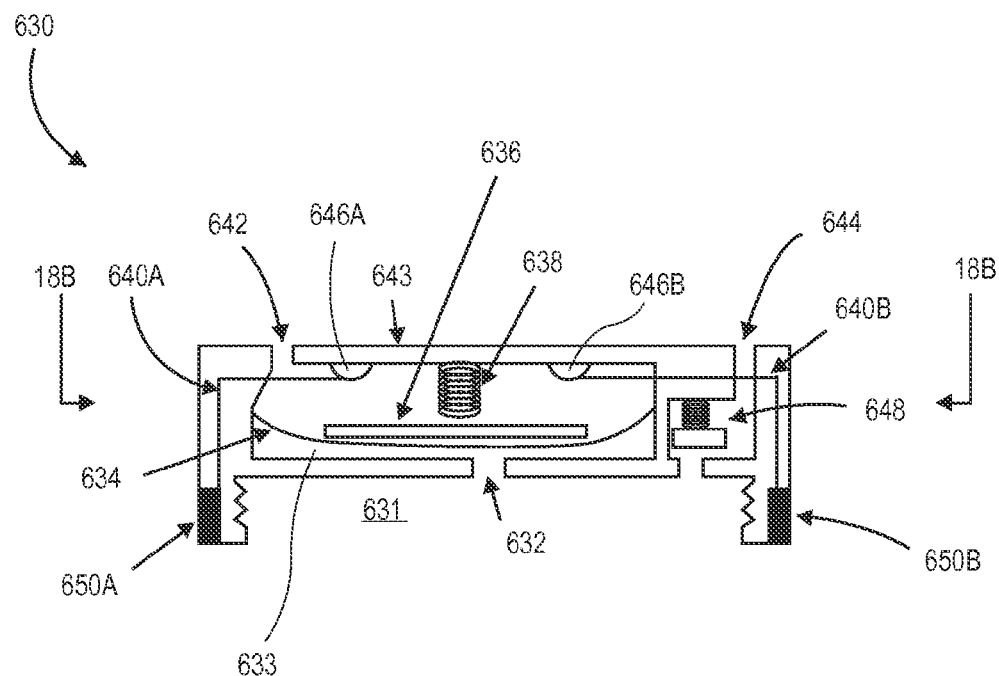
FIGS. 18A-18B illustrate a side view and top view, respectively, the cleaning case of FIG. 17.

Referring to FIG. 18A, certain components and additional features of the embodiment of the cleaning case illustrated in FIG. 17 are shown. FIG. 18A shows a side view of cap 630 of the cleaning case shown in FIG. 17.

As explained above, when a peroxide-based cleaning solution and catalyst are used, an oxidation-reduction reaction occurs. During this reaction, oxygen bubbles are generated at the catalyst. These bubbles float to the surface of the solution, whereupon oxygen gas is released. If the cap makes a reasonably gas-tight seal onto the cylinder, pressure in the headspace above the solution will increase as gas is released. Fresh solutions and catalysts will generate more gas than old ones. Messages informing a user about the quality and useful life of the cleaning solution and catalyst can be generated using these concepts.

Still referring to FIG. 18A, cap 630 includes several components which can measure the pressure of gas generated by the reaction of a peroxide with a catalyst, i.e. a reaction sensor in the form of a pressure sensor. Internal port 632 allows gas from headspace 631 to enter bladder 633 where it pushes against diaphragm 634. As the pressure builds, diaphragm 634 pushes against shorting bar 636, which is disposed against spring 638 towards cap top 643 until it contacts pins 646A and 646B. Pins 646A and 646B are connected to wires 640A and 640B, respectively, which are connected to case contacts 650A and 650B, respectively.

After a cleaning cycle is initiated and case 610 is placed in caddy 680 (FIG. 17), gas is generated by the chemical reaction. When shorting bar 636, which is electrically conductive, contacts pins 646A-B, an electrical connection is made between the two pins and a connecting to a logic chip is completed. Thus, a signal can be sent to a processing device so that a message can be displayed and/or a timer can also be started to display messages at a later time. For example, upon shorting bar 636 making a connection to pins 646A and 646B, a message such as "Your Contact Lenses are Being Cleaned" can be displayed, e.g. in display 154 (FIG. 17). At this time a timer can count to a specified time, e.g. 6 hours, at which time a message such as "Your Contact Lenses are Clean and Ready for Use" can be displayed. Alternatives can be easily envisaged.

Referring again to FIG. 18A, external port 642 allows air to escape as diaphragm 634 and shorting bar 636 are disposed towards cap top 643. Cap 630 may also include an overflow port 644 opened by overflow valve 648. In some cases when the pressure in the headspace exceeds a certain amount, such a system can allow excess gas to escape from the headspace.

Figure 18B:
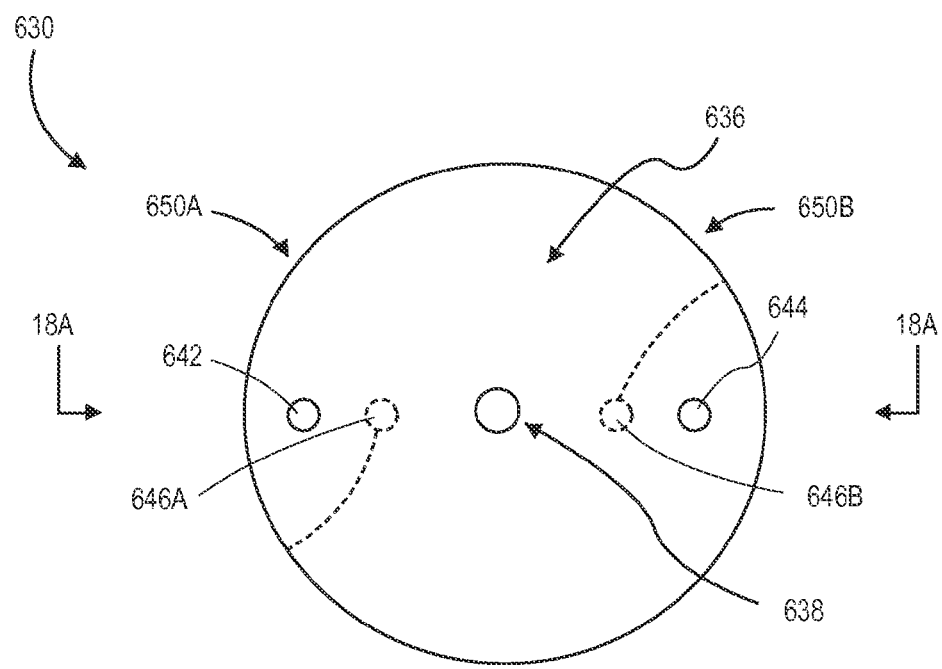

FIG. 18B shows a top-down view of the cap shown in FIG. 18A. This view shows shorting bar 636, spring 638, external port 642, overflow port 644, pins 646A-B, and case contacts 650A-B. In the embodiment shown in FIGS. 18A-B, the shorting bar 636 is shown as a disc, however it may take any other appropriate shapes, such as that of a pin or rod, an oval, etc.

The examples above describe in detail embodiments in which the temperature of the solution is measured with a temperature sensor, and another embodiment in which pressure of gas generated by a reaction of peroxide with a catalyst is measured by a pressure sensor. However, this disclosure encompasses additional embodiments wherein other ways of measuring or sensing a property using a sensor may be used. Such sensors may be, for example and without limitation, an electronic sensor (which includes a sensor of conductivity, voltage, or other electronic properties, e.g. between two electrodes), a sound sensor, an optical sensor, or a gas sensor. For example, in one embodiment, a caddy may include two electrodes (the catalyst can be one electrode) which contact the cleaning solution. Differences in the conductivity or voltage over time as the reaction of peroxide with the catalyst progresses can be measured using a reaction sensor and used to initiate a timer or display one or more messages, as described above. In other embodiments, other types of sensors may be used to drive similar processes.

Also provided are methods of monitoring patient compliance with a protocol for cleaning a medical device with a cleaning solution, the methods comprising obtaining data by measuring a property of the cleaning solution or a nearby area or the medical device, and displaying one or more messages according to the data. The data obtained from the measurements ("measurement data") may be compared to preset data stored in memory, and the one or more message may be based on a comparison between the measurement data and the preset data. In some embodiments, the data may be provided to a medical professional. For example, in one method, data from measuring the temperature or temperature profile of a cleaning case may be obtained and compared to preset data, e.g. an acceptable temperature profile range (see discussion of FIG. 5, above). If the measurement data is within the acceptable range, a message such as "Disinfection working properly" can be displayed; if not, then a message such as "Disinfection unsuccessful" can be displayed. Data for a series of cleaning events can be stored over time. This data can be provided to or accessed by the user or a healthcare professional such as, in embodiments where the medical device is a contact lens, an optician. For example, the user or medical professional can access the data with a computer, smartphone, or similar computing device. The data may provide a history of the user's cleaning regimens over a certain time, e.g. six months or a year. With this method, the user and optician can monitor and improve compliance with the cleaning protocol.

Any of the apparatus or systems (e.g. caddies) or methods described herein may have the following additional features or components. They may include a first sensor and a second sensor, wherein the first and second sensors are each one of the sensors described above (thermal, optical, etc.) and wherein the first sensor measures a property relating to the oxidation/reduction reaction of the peroxide and catalyst (e.g. temperature changes, conductivity or voltage changes between electrodes, pressure, sound, etc.) and the second sensor measures a certain "signature" of the solution. The signature may be, for example, a unique optical absorptivity of one supplier's cleaning solution absent in other cleaning solutions. The caddy can be programmed to operate only when this "signature" is detected. Thus, a caddy can be made to operate only when a particular supplier's cleaning solution is used. In some embodiments, the apparatus or system can include a selector switch or similar input device in which the user selects the frequency at which they replace their contact lenses. For example, a selector switch can include options for daily, weekly, bi-weekly, or monthly replacement. Such a selection, which can also be made with a computer or similar device, can send a signal to the processing device so that a message can be displayed suggesting the user replace his or her contact lenses.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. This, in the context of this disclosure, although a temperature sensor and a pressure sensor may not be structural equivalents, in that a temperature sensor may measure temperature using an infrared detector and a pressure sensor may measure pressure of a gas, in the context of measuring a property of a cleaning solution, the area near a cleaning or one or more of the medical devices being cleaned, a temperature sensor and a pressure sensor may be equivalent structures.

What is claimed is:

1. A contact lens cleaning system comprising:
   a contact lens holder;
   a vial adapted to contain the contact lens holder and a cleaning solution;
   a catalyst capable of neutralizing the cleaning solution;
   a sensor capable of providing data on a rate of neutralization of the cleaning solution;
   a processing device in communication with the sensor to receive the rate of neutralization data from the sensor; and
   a display in communication with the processing device, the processing device being adapted to operate the display to provide cleaning efficacy information based on the rate of neutralization data.

2. The system of claim 1 wherein the sensor is a temperature sensor.

3. The system of claim 2 wherein the temperature sensor is disposed in a cap covering the vial.

4. The system of claim 2 wherein the temperature sensor is disposed outside of the vial.

5. The system of claim 2 wherein the processing device is adapted to determine a temperature change rate from the rate of neutralization data.

6. The system of claim 5 wherein the processing device is further adapted to determine cleaning efficacy by comparing the temperature change rate to a theoretical temperature change rate.

7. The system of claim 6 further comprising an ambient temperature sensor disposed outside of the vial and adapted to measure a temperature of air surrounding the vial, the processing device being further adapted to determine cleaning efficacy using a temperature signal from the ambient temperature sensor to correct for ambient temperature affect to the approximate rate of temperature change as compared to the theoretical temperature change rate.

8. The system of claim 1 further comprising a use counter communicating with the processing device, the processing device being further adapted to display information corresponding to the number of cleaning uses of the cleaning system.

9. The system of claim 1 wherein the sensor is a pressure sensor.

10. The system of claim 1 further comprising a caddy adapted to support the vial.

11. The system of claim 10 wherein the display is disposed within the caddy.

12. The system of claim 1 wherein the display is disposed in a cap on the vial.

13. The system of claim 1 further comprising a solution sensor disposed within the vial, the processing device being further adapted to determine the presence of cleaning solution within the vial based on a signal from the solution sensor.

14. The system of claim 13 wherein the solution sensor comprises an electrode.

15. The system of claim 13 wherein the solution sensor comprises a capacitive sensor.

16. The system of claim 1 wherein the catalyst comprises platinum.

17. The system of claim 1 wherein the cleaning solution comprises hydrogen peroxide.

18. The system of claim 1 wherein the sensor is a conductivity sensor.

19. The system of claim 18 wherein the processing device is adapted to determine a conductivity change rate from the rate of neutralization data.

20. The system of claim 19 wherein the processing device is further adapted to determine cleaning efficacy by comparing the conductivity change rate to a theoretical conductivity change rate.

21. A contact lens cleaning system comprising:
a contact lens holder;
a vial adapted to contain the contact lens holder and a cleaning solution;
a catalyst capable of neutralizing the cleaning solution;
a sensor capable of providing data on a characteristic of the neutralization of the cleaning solution;
a processing device in communication with the sensor to receive the data from the reaction sensor, and determine an approximate rate of neutralization using the data; and
a display in communication with the processing device, the processing device being adapted to operate the display to provide cleaning efficacy information based on the approximate rate of neutralization.

22. The system according to claim 21, wherein the characteristic of the chemical reaction is temperature resulting from heat produced by the neutralization of the cleaning solution, and wherein the sensor is a temperature sensor.

23. The system according to claim 22, wherein the processing device is further adapted to determine cleaning efficacy by comparing the approximate rate of temperature change to a theoretically determined rate of temperature change for the neutralization of the cleaning solution.

24. The system according to claim 23 further comprising an ambient temperature sensor disposed outside of the vial and adapted to measure a temperature of air surrounding the vial, the processing device being further adapted to determine cleaning efficacy using a temperature signal from the ambient temperature sensor to correct for ambient temperature affect to the approximate rate of temperature change as compared to the theoretically determined rate of temperature change.

25. The system according to claim 21, wherein the characteristic of the neutralization of the cleaning solution is pressure resulting from a gas product from the neutralization, and wherein the sensor is a pressure sensor.

26. The system according to claim 25, wherein the processing device is further adapted to determine cleaning efficacy by comparing the approximate rate of pressure change to a theoretically determined rate of pressure change for the neutralization.

27. The system according to claim 21 wherein the catalyst comprises platinum.

28. The system according to claim 21 wherein the cleaning solution comprises hydrogen peroxide.

29. The system according to claim 21, wherein the characteristic of the neutralization of the cleaning solution is conductivity resulting from the neutralization of the cleaning solution, and wherein the sensor is a conductivity sensor.

30. The system according to claim 29, wherein the processing device is further adapted to determine cleaning efficacy by comparing the approximate rate of conductivity change to a theoretically determined rate of conductivity change for the neutralization of the cleaning solution.

31. A contact lens cleaning system comprising:
a contact lens holder;
a vial adapted to contain the contact lens holder and a cleaning solution;
a catalyst capable neutralizing the cleaning solution;
a conductivity sensor capable of generating conductivity data related to a rate of neutralization of the cleaning solution;
a processing device in communication with the conductivity sensor to obtain the conductivity data and determine an approximate rate of neutralization using the conductivity data; and
a display in communication with the processing device, the processing device being adapted to operate the display to provide cleaning efficacy information based on the approximate rate of neutralization.

* * * * *